(12) United States Patent
Griesgraber

(10) Patent No.: US 8,178,539 B2
(45) Date of Patent: May 15, 2012

(54) SUBSTITUTED 3,4,6,7-TETRAHYDRO-5H-1,2A,4A,8-TETRAAZACYCLOPENTA[CD] PHENALENES AND METHODS

(75) Inventor: George W. Griesgraber, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 502 days.

(21) Appl. No.: 12/440,295

(22) PCT Filed: Sep. 6, 2007

(86) PCT No.: PCT/US2007/019430
§ 371 (c)(1),
(2), (4) Date: Mar. 6, 2009

(87) PCT Pub. No.: WO2008/030511
PCT Pub. Date: Mar. 13, 2008

(65) Prior Publication Data
US 2010/0173906 A1   Jul. 8, 2010

Related U.S. Application Data

(60) Provisional application No. 60/824,695, filed on Sep. 6, 2006.

(51) Int. Cl.
*A61K 31/4965* (2006.01)
*A61K 31/497* (2006.01)
(52) U.S. Cl. ............... 514/255.05; 514/252.1; 544/343
(58) Field of Classification Search .............. 544/343; 514/252.1, 255.05
See application file for complete search history.

(56) References Cited

U.S. PATENT DOCUMENTS

| 3,314,941 | A | 4/1967 | Littell et al. |
|---|---|---|---|
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,238,944 | A | 8/1993 | Wick et al. |
| 5,266,575 | A | 11/1993 | Gerster |
| 5,268,376 | A | 12/1993 | Gester |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,444,065 | A | 8/1995 | Nikolaides et al. |
| 5,446,153 | A | 8/1995 | Lindstrom et al. |
| 5,482,936 | A | 1/1996 | Lindstrom |
| 5,494,916 | A | 2/1996 | Lindstrom et al. |
| 5,525,612 | A | 6/1996 | Gerster |
| 5,627,281 | A | 5/1997 | Nikolaides et al. |
| 5,644,063 | A | 7/1997 | Lindstrom et al. |
| 5,648,516 | A | 7/1997 | Nikolaides et al. |
| 5,693,811 | A | 12/1997 | Lindstrom |
| 5,714,608 | A | 2/1998 | Gerster |
| 5,741,908 | A | 4/1998 | Gerster et al. |
| 5,756,747 | A | 5/1998 | Gerster et al. |
| 5,886,006 | A | 3/1999 | Nikolaides et al. |
| 5,939,090 | A | 8/1999 | Beaurline et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,194,425 | B1 | 2/2001 | Gerster et al. |
| 6,200,592 | B1 | 3/2001 | Tomai et al. |
| 6,245,776 | B1 | 6/2001 | Skwierczynski et al. |
| 6,331,539 | B1 | 12/2001 | Crooks et al. |
| 6,365,166 | B2 | 4/2002 | Beaurline et al. |
| 6,376,669 | B1 | 4/2002 | Rice et al. |
| 6,440,992 | B1 | 8/2002 | Gerster et al. |
| 6,451,810 | B1 | 9/2002 | Coleman et al. |
| 6,486,168 | B1 | 11/2002 | Skwierczynski et al. |
| 6,514,985 | B1 | 2/2003 | Gerster et al. |
| 6,518,265 | B1 | 2/2003 | Kato et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 6,610,319 | B2 | 8/2003 | Tomai et al. |
| 6,627,638 | B2 | 9/2003 | Gerster et al. |
| 6,627,640 | B2 | 9/2003 | Gerster et al. |
| 6,630,588 | B2 | 10/2003 | Rice et al. |
| 6,656,938 | B2 | 12/2003 | Crooks et al. |
| 6,660,735 | B2 | 12/2003 | Crooks et al. |

(Continued)

FOREIGN PATENT DOCUMENTS

EP    0 394 026    10/1990

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan et al., "Automated Bioassay of Interferons in Micro-test Plates.", *Biotechniques*, Jun./Jul., 78, 1983.
Testerman et al., "Cytokine Induction by the Immunomodulators Imiquimod and S-27609.", *Journal of Leukocyte Biology*, vol. 58, pp. 365-372, Sep. 1995.

(Continued)

*Primary Examiner* — Shengjun Wang

(57) ABSTRACT

Substituted 3,4,6,7-tetrahydro-5H-1,2a,4a,8-tetraazacyclopenta[cd]phenalene-9-amines, pharmaceutical compositions containing the compounds or salts thereof, intermediates, methods of making the compounds or salts thereof, and methods of use of these compounds or salts thereof or pharmaceutical compositions as immunomodulators, for inducing cytokine biosynthesis in animals and in the treatment of diseases including viral and neoplastic diseases, are disclosed.

20 Claims, No Drawings

U.S. PATENT DOCUMENTS

| | | | |
|---|---|---|---|
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 | 8/2006 | Hays et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,968,562 B2 | 6/2011 | Skwierczynski et al. |
| 7,968,563 B2 | 6/2011 | Kshirsager et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0155767 A1 | 7/2007 | Radmer et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0287725 A1 | 12/2007 | Moser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |

| | | |
|---|---|---|
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |
| 2011/0021554 A1 | 1/2011 | Stoesz et al. |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/003064 | 1/2005 |
| WO | WO 2006/028451 | 3/2006 |
| WO | WO 2006/063072 | 6/2006 |
| WO | WO2006086633 | 8/2006 |
| WO | WO2006091567 | 8/2006 |
| WO | WO 2006/121528 | 11/2006 |
| WO | WO 2007/030775 | 3/2007 |

OTHER PUBLICATIONS

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatves as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

SUBSTITUTED 3,4,6,7-TETRAHYDRO-5H-1,2A,4A,8-TETRAAZACYCLOPENTA[CD] PHENALENES AND METHODS

This application is a National Stage Application of International Application No. PCT/US2007/019430, filed Sep. 6, 2007, which claims priority to U.S. Provisional Patent Application No. 60/824,695, filed Sep. 6, 2006 (expired).

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a new class of compounds, that are useful in inducing cytokine biosynthesis in animals. Such compounds are substituted 3,4,6,7-tetrahydro-5H-1,2a,4a,8-tetraazacyclopenta[cd]phenalene-9-amines of the following Formula I:

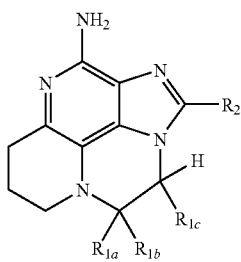

I and, more particularly, compounds of the following Formulas Ia, II, and IIa:

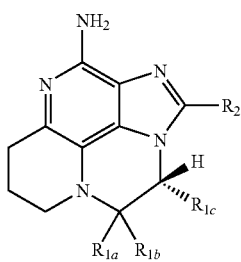

Ia

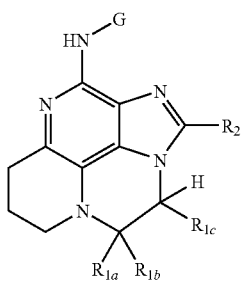

II

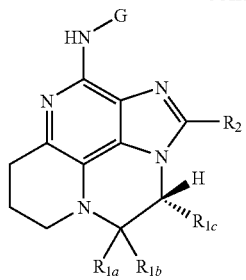

IIa wherein $R_{1a}$, $R_{1b}$, $R_{1c}$, $R_2$, and G are as defined below; and include pharmaceutically acceptable salts thereof.

The compounds and salts of Formulas I, Ia, II, and IIa are useful as immune response modifiers (IRMs) due to their ability to modulate cytokine biosynthesis (e.g., induce the biosynthesis or production of one or more cytokines) or otherwise modulate the immune response when administered to animals. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

The invention further provides pharmaceutical compositions containing an effective amount of the compounds or salts of Formulas I, Ia, II, and IIa.

In another aspect, the present invention provides methods of inducing cytokine biosynthesis in animal cells, treating a viral disease in an animal, and/or treating a neoplastic disease in an animal by administering to the animal one or more compounds of the Formulas I, Ia, II, IIa, and/or pharmaceutically acceptable salts thereof.

In another aspect, the invention provides methods of synthesizing the compounds of Formulas I, Ia, II, IIa, and intermediate compounds useful in the synthesis is of these compounds.

As used herein, "a", "an", "the", "at least one", and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I, Ia, II, and IIa:

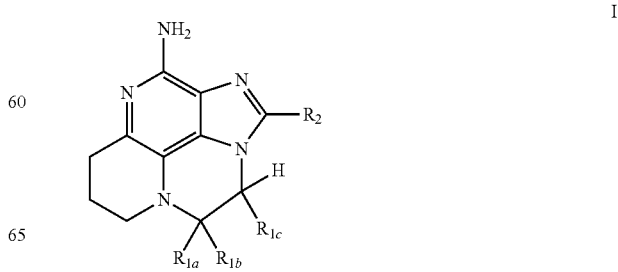

I

-continued

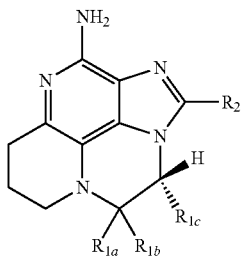

Ia

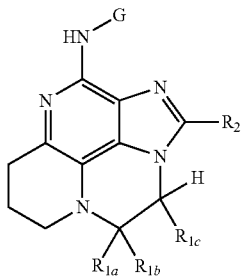

II

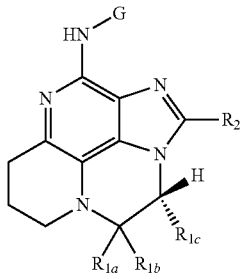

IIa wherein $R_{1a}$, $R_{1b}$, $R_{1c}$, $R_2$, and G are as defined below; and include pharmaceutically acceptable salts thereof.

In one embodiment, the present invention provides a compound of Formula I:

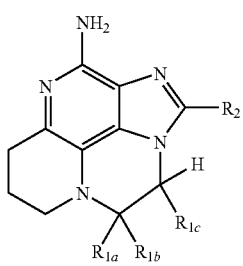

I wherein:

$R_{1a}$ and $R_{1b}$ are independently selected from the group consisting of hydrogen, $C_{1-6}$ alkyl, 1-hydroxy-1-methylethyl, 1-(methylsulfonylamino)-1-methylethyl, 3-(methylsulfonylamino)propyl and 1-fluoro-1-methylethyl; or $R_{1a}$ and $R_{1b}$, together with the carbon atom to which they are attached, form a ring selected from the group consisting of cyclopropane, cyclobutane, cyclopentane, cyclohexane, oxetane, tetrahydrofuran, and tetrahydropyran;

$R_{1c}$ is selected from the group consisting of:
—X—$R_4$,
—X—Y—$R_4$,
—X—Y—X'—Y—$R_4$, and
—X—$R_5$;

$R_2$ is selected from the group consisting of hydrogen, alkyl, alkoxyalkyl, and hydroxyalkyl;

X is alkylene optionally interrupted by one or more —O— groups, and optionally substituted by a hydroxy or methoxy group;

X' is selected from the group consisting of alkylene, arylene, heteroarylene, and heterocyclylene wherein the alkylene group can be optionally interrupted or terminated by arylene, heteroarylene or heterocyclylene and optionally interrupted by one or more —O— groups;

Y is selected from the group consisting of:
—O—,
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,
—O—N($R_8$)-Q-,
—O—N=C($R_4$)—,
—C(=N—O—$R_8$)—,
—CH(—N(—O—$R_8$)-Q-$R_4$)—,

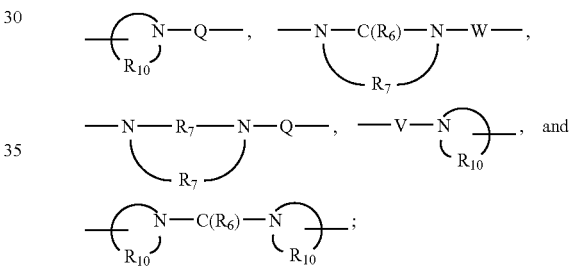

$R_4$ is selected from the group consisting of hydrogen, alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;

$R_5$ is selected from the group consisting of:

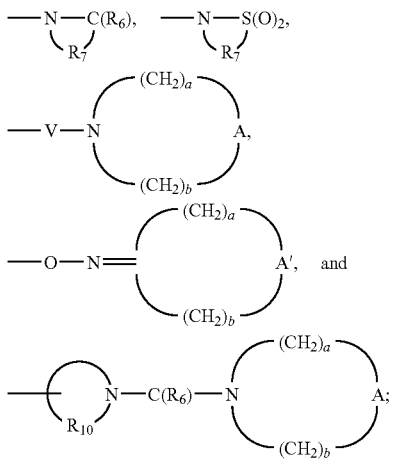

$R_6$ is selected from the group consisting of =O and =S;
$R_7$ is $C_{2-7}$ alkylene;
$R_8$ is selected from the group consisting of hydrogen, $C_{1-10}$alkyl, $C_{2-10}$alkenyl, hydroxy-$C_{1-10}$alkylenyl, $C_{1-10}$ alkoxy-$C_{1-10}$alkylenyl, aryl-$C_{1-10}$alkylenyl, and heteroaryl-$C_{1-10}$alkylenyl;
$R_9$ is selected from the group consisting of hydrogen and alkyl;
$R_{10}$ is $C_{3-8}$ alkylene;
A is selected from the group consisting of —$CH_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —$CH_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≤7;
with the proviso that X can also be a bond when:
$R_4$ is bonded to X; or
Y is bonded to X and Y is —C($R_6$)—, —C($R_6$)—O—, —C($R_6$)—N($R_8$)—, —C($R_6$)—N(O$R_9$)—, —C(=N—O—$R_8$)—, —CH(—N(—O—$R_8$)-Q-$R_4$)—,

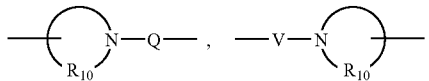

wherein V is —C($R_6$)—, or

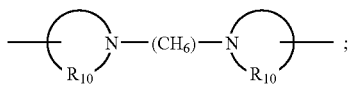

or
$R_5$ is bonded to X and $R_5$ is

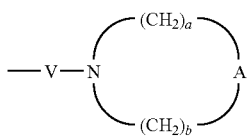

wherein V is —C($R_6$)— or

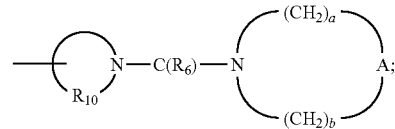

or a pharmaceutically acceptable salt thereof.

In one preferred embodiment, the present invention provides a compound of Formula Ia:

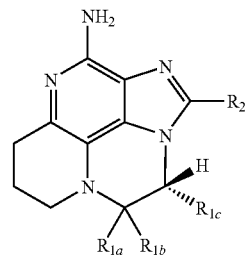

Ia wherein:
$R_{1a}$, $R_{1b}$, $R_{1c}$, and $R_2$ are defined as in Formula I above;
or a pharmaceutically acceptable salt thereof.

In another embodiment, the present invention provides a compound of Formula II:

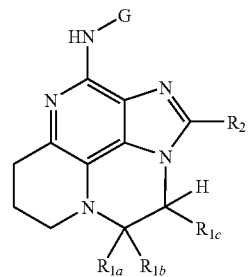

II wherein:
$R_{1a}$, $R_{1b}$, $R_{1c}$, and $R_2$ are defined as in Formula I above;
G is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(O$C_{1-4}$alkyl)$Y_0$,
—$CH_2Y_1$, and
—CH($CH_3$)$Y_1$;
R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an α-amino acid selected from the group consisting of racemic, D-, and L-amino acids;

Y' is selected from the group consisting of hydrogen, C$_{1-6}$ alkyl, and benzyl;

Y$_0$ is selected from the group consisting of C$_{1-6}$ alkyl; carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl; and Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;

or a pharmaceutically acceptable salt thereof.

In another embodiment, the present invention provides a compound of Formula IIa:

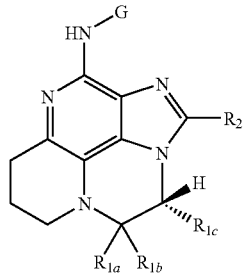

IIa wherein

R$_{1a}$, R$_{1b}$, R$_{1c}$, and R$_2$ are defined as in Formula I above; and

G is defined as in Formula II above;

or a pharmaceutically acceptable salt thereof.

The term "animal" as used herein includes animals such as, for example, humans, non-human primates, rodents, dogs, cats, horses, pigs, sheep, goats, cattle, and poultry.

As used herein, the terms "alkyl", "alkenyl", and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms "alkylenyl" and "alkenylenyl" are used when "alkylene" and "alkenylene", respectively, are substituted. For example, an arylalkylenyl group comprises an alkylene moiety to which an aryl group is attached.

Unless otherwise indicated, the term "halogen" refers to a halogen atom or one or more halogen atoms.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. In some embodiments, the term "heteroaryl" includes one ring that contains 2-5 carbon atoms, 1-3 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. In some embodiments, the term "heterocyclyl" includes one ring that contains 2-5 carbon atoms, 1-3 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, when two R$_7$ groups are present, each R$_7$ group is independently selected. In another example, when more than one Y group is present and each Y group contains one or more $R_8$ groups, then each Y group is independently selected, and each $R_8$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, the invention specifically includes enantiomerically pure compounds, mixtures of enantiomers in any ratio, as well as racemic compounds. Ratios of a compound to its enantiomer include, for example, 50:50 or higher, 90:10 or higher, 95:5 or higher, 99:1 or higher, 99.9:0.1 or higher, or 100:0. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Q, X, X', Y, Y', $R_4$, $R_{1a}$, $R_{1b}$, $R_{1c}$, $R_2$, G, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, including embodiments of Formulas I, Ia, II, or IIa, $R_{1a}$ and $R_{1b}$ are independently selected from the group consisting of hydrogen, $C_{1-6}$ alkyl, 1-hydroxy-1-methylethyl, 1-(methylsulfonylamino)-1-methylethyl, 3-(methylsulfonylamino)propyl and 1-fluoro-1-methylethyl; or $R_{1a}$ and $R_{1b}$, together with the carbon atom to which they are attached, form a ring selected from the group consisting of cyclopropane, cyclobutane, cyclopentane, cyclohexane, oxetane, tetrahydrofuran, and tetrahydropyran. For certain of these embodiments, $R_{1a}$ and $R_{1b}$ are independently selected from the group consisting of hydrogen, $C_{1-6}$ alkyl, 1-hydroxy-1-methylethyl, 1-(methylsulfonylamino)-1-methylethyl, 3-(methylsulfonylamino)propyl and 1-fluoro-1-methylethyl. For certain of these embodiments, $R_{1a}$ and $R_{1b}$ are independently selected from the group consisting of hydrogen and $C_{1-6}$ alkyl. For certain of these embodiments, $R_{1a}$ and $R_{1b}$ are independently selected from the group consisting of hydrogen and methyl. For certain of these embodiments, $R_{1a}$ and $R_{1b}$ are both hydrogen or both methyl. Alternatively, for certain of these embodiments, $R_{1a}$ and $R_{1b}$ join together to form a ring selected from the group consisting of cyclopropane, cyclobutane, cyclopentane, cyclohexane, oxetane, tetrahydrofuran, and tetrahydropyran. For certain of these embodiments, $R_{1a}$ and $R_{1b}$ join together to form a tetrahydropyran ring.

For certain embodiments, including any one of the above embodiments of Formulas I, Ia, II, or IIa, $R_{1c}$ is selected from the group consisting of —X—$R_4$, —X—Y—$R_4$, —X—Y—X'—Y—$R_4$, and —X—$R_5$. For certain of these embodiments, $R_{1c}$ is —X—$R_4$. For certain of these embodiments, $R_4$ in —X—$R_4$ is alkyl which is unsubstituted or substituted by one or more substituents selected from the group consisting of halogen, hydroxy, and alkoxy. For certain of these embodiments, $R_4$ is $C_{1-3}$ alkyl optionally substituted by hydroxy or one or more fluorine atoms. For certain of these embodiments, X is a bond or alkylene. For certain of these embodiments, X is a bond. For certain of these embodiments, $R_{1c}$ is methyl. Alternatively, for certain of these embodiments, X is —$CH_2$—. Alternatively, for certain of these embodiments, except where X is a bond or alkylene, X is $C_{1-4}$ alkylene substituted by a hydroxy or methoxy group. Alternatively, for certain of these embodiments, except where X is a bond or alkylene, or $C_{1-4}$ alkylene substituted by a hydroxy or methoxy group, X is alkylene optionally interrupted by one or more —O— groups. For certain of these embodiments, X is $C_{2-3}$ alkylene interrupted by one —O— group.

For certain embodiments, including any one of the above embodiments of Formulas I, Ia, II, or IIa, except where $R_{1c}$ is —X—$R_4$, $R_{1c}$ is —X—Y—$R_4$.

For certain embodiments, including any one of the above embodiments of Formulas I, Ia, II, or IIa, except where $R_{1c}$ is —X—$R_4$ or —X—Y—$R_4$, $R_{1c}$ is —X—Y—X'—Y—$R_4$.

For certain embodiments, including any one of the above embodiments of Formulas I, Ia, II, or IIa, except where $R_{1c}$ is —X—$R_4$, —X—Y—$R_4$, or —X—Y—X'—Y—$R_4$, $R_{1c}$ is —X—$R_5$.

For certain embodiments, including any one of the above embodiments of Formulas I, Ia, II, or IIa where $R_{1c}$ is —X—Y—$R_4$ or —X—Y—X'—Y—$R_4$, Y is —C(O)—, —S(O)$_2$—, —N($R_8$)-Q-, or —C(O)—NH—. For certain of these embodiments where Y is —N($R_8$)-Q-, Q is —C(O)—, —S(O)$_2$—, —S(O)$_2$—N($R_8$)—, or —C(O)—N($R_8$)—. For certain of these embodiments, $R_4$ in Y—$R_4$ is alkyl, aryl, arylalkylenyl, or heteroaryl, wherein aryl, arylalkylenyl, and heteroaryl are optionally substituted by alkyl.

Alternatively, for certain embodiments, including any one of the above embodiments of Formulas I, Ia, II, or IIa where $R_{1c}$ is —X—Y—$R_4$, Y is —S—, —S(O)$_2$—, or N($R_8$)-Q- wherein Q is a bond, —S(O)$_2$—, —C(O)—, —C(O)—O—, —C(O)—N($R_8$)—, —C(S)—N($R_8$)—, or —S(O)$_2$—N($R_8$)—; each $R_8$ is independently selected from the group consisting of hydrogen, $C_{1-4}$ alkyl, hydroxy$C_{1-4}$ alkyl, and $C_{1-4}$ alkoxy$C_{1-4}$alkyl; and $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino. For certain of these embodiments, Y is —NH—S(O)$_2$—, —NH—C(O)—, —NH—S(O)$_2$—N($R_8$)—, —NH—C(O)—N($R_8$)—, —NH—C(S)—N($R_8$)—, —NH—C(O)—O—, or —N($R_8$)—; and $R_8$ is hydrogen, methyl, ethyl, 2-hydroxyethyl, or 2-methoxyethyl. Alternatively, for certain of these embodiments, Y is —S— or —S(O)$_2$—; and $R_4$ is alkyl or aryl.

For certain of these embodiments, including any one of the above embodiments where $R_{1c}$ is —X—Y—$R_4$, X is $C_{1-3}$ alkylene optionally substituted by a hydroxy or methoxy group. For certain of these embodiments, X is —(CH$_2$)$_{1-3}$—. Alternatively, for certain of these embodiments, X is $C_{2-3}$ alkylene substituted by one hydroxy group.

Alternatively, for certain embodiments, including any one of the above embodiments of Formulas I, Ia, II, or IIa where $R_{1c}$ is —X—Y—$R_4$, Y is

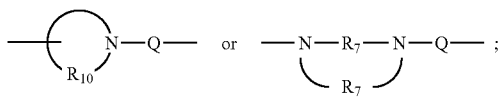

Q is a bond, —C(O)—, —S(O)$_2$—, —S(O)$_2$—, —S(O)$_2$—N($R_8$)—, —C(O)—N($R_8$)—, C(S)—N($R_8$)—, or —C(O)—O—; $R_7$ is $C_{2-3}$ alkylene; $R_8$ is hydrogen or $C_{1-4}$ alkyl; $R_{10}$ is $C_{4-6}$ alkylene; and $R_4$ in Y—$R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, and haloalkyl. For certain of these embodiments, Y is

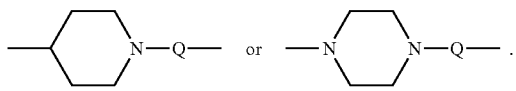

For certain of these embodiments, X is a bond or —CH$_2$—, and Y is

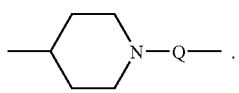

Alternatively, for certain of these embodiments, X is a —CH$_2$— or —(CH$_2$)$_2$—, and Y is

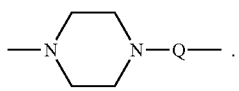

For certain embodiments, including any one of the above embodiments where X can be alkylene, X is $C_{1-4}$ alkylene.

For certain embodiments, including any one of the above embodiments of Formulas I, Ia, II, or IIa, $R_2$ is selected from the group consisting of hydrogen, alkyl, alkoxyalkyl, and hydroxyalkyl. For certain of these embodiments, $R_2$ is selected from the group consisting of hydrogen, $C_{1-4}$ alkyl, $C_{1-4}$ alkoxy$C_{1-4}$ alkyl, and hydroxy$C_{1-4}$ alkyl. For certain of these embodiments, $R_2$ is selected from the group consisting of methyl, ethyl, n-propyl, n-butyl, ethoxymethyl, hydroxymethyl, and 2-methoxyethyl.

For certain embodiments, $R_4$ is selected from the group consisting of hydrogen, alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl.

For certain embodiments, $R_4$ is alkyl which is unsubstituted or substituted by one or more substituents selected from the group consisting of halogen, hydroxy, and alkoxy.

For certain embodiments, $R_4$ is $C_{1-3}$ alkyl optionally substituted by hydroxy or one or more fluorine atoms.

For certain embodiments, $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, haloalkyl, and dialkylamino.

For certain embodiments, $R_4$ is hydrogen, alkyl, aryl, arylalkylenyl, heteroaryl, or heterocyclyl wherein alkyl, aryl, arylalkylenyl, heteroaryl, and heterocyclyl are unsubstituted or substituted by one or more substituents independently selected from the group consisting of hydroxy, halogen, alkoxy, alkyl, and haloalkyl.

For certain embodiments, $R_4$ is alkyl, aryl, arylalkylenyl, or heteroaryl, wherein aryl, arylalkylenyl, and heteroaryl are optionally substituted by alkyl.

For certain embodiments, $R_4$ is alkyl or aryl.

For certain embodiments, $R_4$ is phenyl.

For certain embodiments, $R_5$ is selected from the group consisting of:

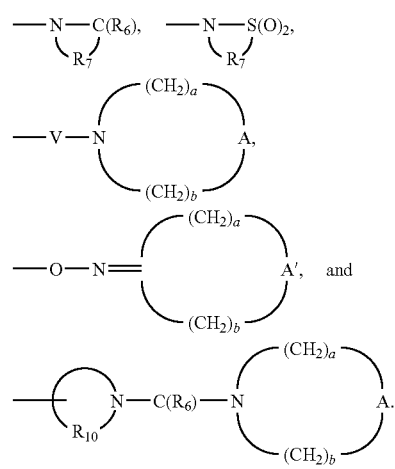

For certain embodiments, $R_5$ is selected from the group consisting of

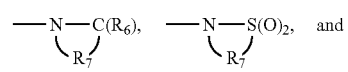

-continued

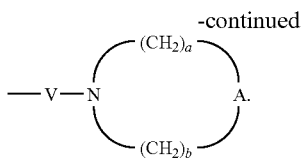

For certain embodiments, $R_5$ is

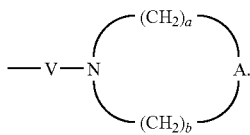

For certain of these embodiments, A is —$CH_2$—, —O—, or —N(-Q-$R_4$)—, and V is —C(O)—. For certain of these embodiments, A is —$CH_2$—, and V is —C(O)—. Alternatively, V is N($R_8$)—C($R_6$)—; A is —O—; a and b are each 2 or 3; and $R_8$ is hydrogen or $C_{1-4}$ alkyl.

For certain embodiments, $R_6$ is selected from the group consisting of =O and =S.

For certain embodiments, $R_6$ is =O.

For certain embodiments, $R_7$ is $C_{2-7}$ alkylene.

For certain embodiments, $R_7$ is $C_{2-3}$ alkylene.

For certain embodiments, $R_7$ is propylene.

For certain embodiments, $R_8$ is selected from the group consisting of hydrogen, $C_{1-10}$ alkyl, $C_{2-10}$ alkenyl, hydroxy$C_{1-10}$ alkylenyl, $C_{1-10}$alkoxy$C_{1-10}$alkylenyl, aryl $C_{1-10}$ alkylenyl, and heteroaryl$C_{1-10}$ alkylenyl.

For certain embodiments, $R_8$ is selected from the group consisting of hydrogen, $C_{1-4}$alkyl, hydroxy$C_{1-4}$ alkylenyl, and $C_{1-4}$ alkoxy$C_{1-4}$ alkylenyl.

For certain embodiments, $R_8$ is hydrogen or $C_{1-4}$ alkyl.

For certain embodiments, $R_8$ is hydrogen or methyl.

For certain embodiments, $R_8$ is hydrogen.

For certain embodiments, $R_9$ is selected from the group consisting of hydrogen and alkyl.

For certain embodiments, $R_9$ is alkyl.

For certain embodiments, $R_9$ is hydrogen.

For certain embodiments, $R_{10}$ is $C_{3-8}$ alkylene.

For certain embodiments, $R_{10}$ is $C_{4-6}$ alkylene.

For certain embodiments, $R_{10}$ is pentylene.

For certain embodiments, A is selected from the group consisting of —$CH_2$—, —O—, —C(O)—, —S(O)$_{0-2}$—, and —N(-Q-$R_4$)—.

For certain embodiments, A is —$CH_2$—, —O—, or —N (-Q-$R_4$)—.

For certain embodiments, A is —O—.

For certain embodiments, A is —$CH_2$—.

For certain embodiments, A is —N(-Q-$R_4$)—.

For certain embodiments, A' is selected from the group consisting of —O—, —S(O)$_{0-2}$—, —N(-Q-$R_4$)—, and —$CH_2$—.

For certain embodiments, A' is —O—.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—.

For certain embodiments, Q is —C(O)—, —S(O)$_2$, —S(O)$_2$—N($R_8$)—, or —C(O)—N($R_8$)—.

For certain embodiments, Q is a bond, —S(O)$_2$—, —C(O)—, —C(O)—O—, —C(O)—N($R_8$)—, —C(S)—N($R_8$)—, or —S(O)$_2$—N($R_8$)—, and each $R_8$ is independently selected from the group consisting of hydrogen, $C_{1-4}$ alkyl, hydroxy$C_{1-4}$ alkyl, and $C_{1-4}$ alkoxy$C_{1-4}$alkyl.

For certain embodiments, Q is a bond.

For certain embodiments, V is selected from the group consisting of —C($R_6$)—, —O—C($R_6$)—, —N($R_8$)—C($R_6$)—, and —S(O)$_2$—.

For certain embodiments, V is —C($R_6$)—.

For certain embodiments, V is —C(O)—.

For certain embodiments, V is —N($R_8$)—C($R_6$)—.

For certain embodiments, V is —N($R_8$)—C(O)—.

For certain embodiments, W is selected from the group consisting of a bond, —C(O)—, and —S(O)$_2$—.

For certain embodiments, W is a bond.

For certain embodiments, X is alkylene optionally interrupted by one or more —O— groups, and optionally substituted by a hydroxy or methoxy group.

For certain embodiments, X is a bond or alkylene.

For certain embodiments, X is a bond.

For certain embodiments, X is —$CH_2$—.

For certain embodiments, X is $C_{1-4}$ alkylene substituted by a hydroxy or methoxy group.

For certain embodiments, X is alkylene optionally interrupted by one or more —O— groups.

For certain embodiments, X is $C_{2-3}$ alkylene interrupted by one —O— group.

For certain embodiments, X is $C_{1-3}$ alkylene optionally substituted by a hydroxy or methoxy group.

For certain embodiments, X is $C_{2-3}$ alkylene substituted by one hydroxy group.

For certain embodiments, X is —(CH$_2$)$_{1-3}$—.

For certain embodiments, X is —$CH_2$— or —(CH$_2$)$_2$—.

For certain embodiments, X is a bond or —$CH_2$—.

For certain embodiments, X is $C_{1-4}$ alkylene.

For certain embodiments, X' is selected from the group consisting of alkylene, arylene, heteroarylene, and heterocyclylene wherein the alkylene group can be optionally interrupted or terminated by arylene, heteroarylene or heterocyclylene and optionally interrupted by one or more —O— groups.

For certain embodiments, X' is alkylene.

For certain embodiments, X' is $C_{1-3}$ alkylene.

For certain embodiments, X' is arylene.

For certain embodiments, X' phenylene.

For certain embodiments, X' is selected from the group consisting of $C_{1-3}$ alkylene and phenylene.

For certain embodiments, Y is selected from the group consisting of —O—, —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—, —O—N($R_8$)-Q-, —C(=N—O—$R_8$)—, —CH(—N(—O—$R_8$)-Q-$R_4$)—,

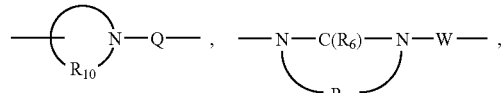

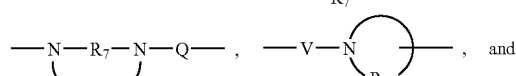

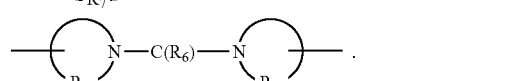

For certain embodiments, Y is selected from the group consisting of —C(O)—, —S(O)$_2$—, —N($R_8$)-Q-, or —C(O)—NH—.

For certain embodiments, Y is selected from the group consisting of —N(R$_8$)—C(O)—, —N(R$_8$)—S(O)$_2$, —N(R$_8$)—S(O)$_2$—N(R$_8$)—, and —N(R$_8$)—C(O)—N(R$_8$)—.

For certain embodiments, Y is —S—, —S(O)$_2$—, —N(R$_5$)—S(O)$_2$—, —N(R$_8$)—C(O)—, —N(R$_8$)—C(O)—O—, —N(R$_8$)—C(O)—N(R$_8$)—, —N(R$_8$)—C(S)—N(R$_8$), or —N(R$_8$)—S(O)$_2$—N(R$_8$)— wherein R$_8$ is hydrogen, C$_{1-4}$ alkyl, hydroxyC$_{1-4}$ alkyl, or C$_{1-4}$ alkoxyC$_{1-4}$ alkyl.

For certain embodiments, Y is —NH—S(O)$_2$—, —NH—C(O)—, —NH—S(O)$_2$—N(R$_8$)—, —NH—C(O)—N(R$_8$)—, —NH—C(S)—N(R$_8$)—, —NH—C(O)—O—, or —N(R$_8$)— wherein R$_8$ is hydrogen, methyl, ethyl, 2-hydroxyethyl, or 2-methoxyethyl.

For certain embodiments, Y is —S— or —S(O)$_2$—.

For certain embodiments, Y is —S(O)$_2$—.

For certain embodiments, Y is

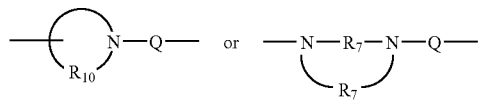

wherein Q is a bond, —C(O)—, —S(O)$_2$—, —S(O)$_2$—N(R$_8$)—, —C(O)—N(R$_8$)—, C(S)—N(R$_8$)—, or —C(O)—O—; R$_7$ is C$_{2-3}$ alkylene; R$_8$ is hydrogen or C$_{1-4}$ alkyl; and R$_{10}$ is C$_{4-6}$ alkylene.

For certain embodiments, Y is

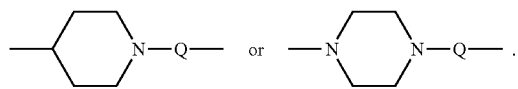

For certain embodiments, Y is

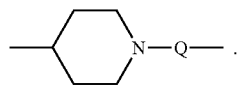

For certain embodiments, Y is number

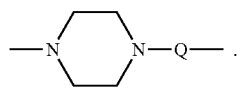

For certain embodiments, a and b are independently integers from 1 to 6 with the proviso that a+b is ≦7.

For certain embodiments, a and b are each 2 or 3.

For certain embodiments, a and b are each 2.

For certain embodiments of the compounds of Formulas I, Ia, or any one of the above embodiments of these Formulas, the —NH$_2$ group can be replaced by an —NH-G group, as shown in the compounds of Formulas II and IIa, to form prodrugs. In such embodiments, G is selected from the group consisting of: —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$. For certain embodiments, G is selected from the group consisting of —C(O)—R', α-aminoacyl, α-aminoacyl-α-aminoacyl, and —C(O)—O—R'. Preferably, R' and R' are independently selected from the group consisting of C$_{1-10}$ alkyl, C$_{3-7}$ cycloalkyl, phenyl, benzyl, and 2-phenylethyl each of which may be unsubstituted or substituted by one or more substitutents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen. Preferably, α-aminoacyl is an α-aminoacyl group derived from an α-amino acid selected from the group consisting of racemic, D-, and L-amino acids. Preferably, Y' is selected from the group consisting of hydrogen, C$_{1-6}$ alkyl, and benzyl. Preferably, Y$_0$ is selected from the group consisting of C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl. Preferably, Y$_1$ is selected from the group consisting of mono-N—C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments of Formula II or IIa, G is selected from the group consisting of —C(O)—R', α-aminoacyl, and —C(O)—O—R'.

For certain embodiments, including any one of the above embodiments of Formula II or IIa, G is selected from the group consisting of —C(O)—R', α-amino-C$_{2-11}$ acyl, and —C(O)—O—R'. α-Amino-C$_{2-11}$ acyl includes α-amino acids containing a total of at least 2 carbon atoms and a total of up to 11 carbon atoms, and may also include one or more heteroatoms selected from the group consisting of O, S, and N.

In some embodiments, the present invention provides a pharmaceutical composition comprising a therapeutically effective amount of a compound or salt of any one of Formulas I, Ia, II, IIa, or any one of the above embodiments and a pharmaceutically acceptable carrier.

In some embodiments, the present invention provides a method of inducing cytokine biosynthesis in an animal comprising administering an effective amount of a compound or salt of any one of Formulas I, Ia, II, IIa, or any one of the above embodiments of these Formulas or administering any one of the above pharmaceutical compositions containing a compound or salt of any one of Formulas I, Ia, II, IIa, or any one of the above embodiments of these Formulas to the animal. For certain of these embodiments, the cytokine is selected from the group consisting of IFN-α, TNF-α, IL-6, IL-10, and IL-12. For certain of these embodiments, the cytokine is IFN-α or TNF-α. For certain of these embodiments, the cytokine is IFN-α.

In some embodiments, the present invention provides a method of treating a viral disease in an animal in need thereof comprising administering a therapeutically effective amount of a compound or salt of any one of Formulas I, Ia, II, IIa, or any one of the above embodiments of these Formulas or administering any one of the above pharmaceutical compositions containing a compound or salt of any one of Formulas I, Ia, II, IIa, or any one of the above embodiments of these Formulas to the animal.

In some embodiments, the present invention provides a method of treating a neoplastic disease in an animal in need thereof comprising administering a therapeutically effective amount of a compound or salt of any one of Formulas I, Ia, II, IIa, or any one of the above embodiments of these Formulas or administering any one of the above pharmaceutical compositions containing a compound or salt of any one of Formulas I, Ia, II, IIa, or any one of the above embodiments of these Formulas to the animal.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*; v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I, wherein $R_{1a}$, $R_{1b}$, $R_{1c}$, and $R_2$ are as defined above; and P is a hydroxy protecting group. In step (1) of Reaction Scheme 1,4-chloro-3-nitro[1,5]naphthyridine is treated with an amino alcohol of Formula X to provide a compound of Formula XI. Several amino alcohols of Formula X are commercially available, such as (S)-1-amino-2-propanol, L-valinol, (S)-2-phenylglycinol, and (S')-2-amino-3-phenyl-1-propanol. Others can be prepared by known synthetic methods; for example, see the methods described in Williams, L. et al., *Tetrahedron*, 52, pp. 11673-11694, (1996) and Genevois-Borella, A. et al., *Tetrahedron Lett.*, 31, pp. 4879-4882 (1990) for the preparation of amino alcohols.

The reaction in step (1) is conveniently carried out by adding the amino alcohol of Formula X to a solution of 4-chloro-3-nitro[1,5]naphthyridine in a suitable solvent such as dichloromethane, optionally in the presence of a tertiary amine such as triethylamine. The reaction can be carried out at ambient temperature or at an elevated temperature such as, for example, the reflux temperature of the solvent.

In step (2) of Reaction Scheme I, the hydroxy group of a 3-nitro[1,5]naphthyridin-4-amine of Formula XI is protected using conventional techniques to provide a 3-nitro[1,5]naphthyridin-4-amine of Formula XII. A number of suitable protecting groups can be used; in particular, protecting groups that would survive the reduction in step (3) are preferred. Suitable protecting groups include but are not limited to silyl groups such as the tert-butyl dimethylsilyl group. The reaction is conveniently carried out by treating the hydroxy-substituted compound of Formula XI with tert-butyldimethylsilyl chloride in the presence of a base such as triethylamine and catalytic 4-(dimethylamino)pyridine (DMAP). The reaction can be carried out in a suitable solvent such as dichloromethane or pyridine at ambient temperature or at an elevated temperature such as, for example, the reflux temperature of the solvent.

Compounds of Formula XII may also be prepared in step (1) of Reaction Scheme if the hydroxy group on a compound of Formula X is protected before the reaction. The protection of the hydroxy group on a compound of Formula X can be carried out as described above in step (2).

In step (3) of Reaction Scheme I, a 3-nitro[1,5]naphthyridin-4-amine of Formula XII is reduced to provide a [1,5]naphthyridine-3,4-diamine of Formula XIII. The reaction can be carried out by hydrogenation using a heterogeneous hydrogenation catalyst such as platinum on carbon. The hydrogenation is conveniently carried out in a Parr apparatus in a suitable solvent such as toluene, methanol, isopropanol, ethyl acetate, or acetonitrile. The reaction can be carried out at ambient temperature.

In step (4) of Reaction Scheme I, a [1,5]naphthyridine-3,4-diamine of Formula XIII is reacted with a carboxylic acid equivalent, which is selected such that it will provide the desired $R_2$ substituent in a 1H-imidazo[4,5-c][1,5]naphthyridine of Formula XIV. Suitable carboxylic acid equivalents include ortho esters, acid halides, imidates, and imidate salts.

The reaction with an acid halide of formula $R_2$—C(O)Cl or $R_2$—C(O)Br may be carried out in two parts, which include (i) adding the acid halide to a solution of a [1,5]naphthyridine-3,4-diamine of Formula XIII in a suitable solvent such as chloroform, dichloromethane, or 1,2-dichloroethane, optionally in the presence of a tertiary amine such as triethylamine to afford an amide intermediate and (ii) cyclizing to provide a 1H-imidazo[4,5-c][1,5]naphthyridine of Formula XIV. The amide intermediate from part (i) can be optionally isolated using conventional techniques. The cyclization in part (ii) may be carried out by heating the amide intermediate from part (i) in a suitable solvent such as toluene. The cyclization in part (ii) can also be carried out in the presence of a base such as triethylamine.

In step (5) of Reaction Scheme I, a 1H-imidazo[4,5-c][1,5]naphthyridine of Formula XIV is oxidized to provide a 1H-imidazo[4,5-c][1,5]naphthyridine-5N-oxide of Formula XV using a conventional oxidizing agent capable of forming N-oxides. The reaction is conveniently carried out by adding 3-chloroperoxybenzoic acid to a solution of a compound of Formula XIV in a solvent such as chloroform or dichloromethane. The reaction can be carried out at ambient temperature.

In step (6) of Reaction Scheme I, a 1H-imidazo[4,5-c][1,5]naphthyridine-5N-oxide of Formula XV is aminated to provide a 1H-imidazo[4,5-c][1,5]naphthyridin-4-amine of Formula XVI. Step (6) involves the activation of an N-oxide of Formula XV by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XV in a suitable solvent such as dichloromethane or chloroform and then adding p-toluenesulfonyl chloride. The reaction can be carried out at ambient temperature.

Alternatively, the oxidation and amination can be carried out as a one-pot procedure without isolating the N-oxide of Formula XV by adding 3-chloroperoxybenzoic acid to a solution of a compound of Formula XIV in a solvent such as dichloromethane or chloroform and then adding ammonium hydroxide and p-toluenesulfonyl chloride.

The amination reaction in step (6) of Reaction Scheme I can alternatively be carried out by treating a 5N-oxide of Formula XV with trichloroacetyl isocyanate followed by hydrolysis of the resulting intermediate to provide a compound of Formula XVI. The reaction is conveniently carried out in two steps by (i) adding trichloroacetyl isocyanate to a solution of a 5N-oxide of Formula XV in a solvent such as dichloromethane and stirring at ambient temperature to provide an isolable amide intermediate. In step (ii), a solution of the intermediate in methanol is treated with a base such as sodium methoxide or ammonium hydroxide at ambient temperature.

In step (7) of Reaction Scheme I, the hydroxy protecting group on a 1H-imidazo[4,5-c][1,5]naphthyridin-4-amine of Formula XVI is removed to reveal the hydroxy group in a product of Formula XVII. The deprotection reaction can be carried out using a variety of conventional methods, depending on the protecting group used. When P is a silyl group such as tert-butyldimethylsilyl, the deprotection can be carried out by treating the 1H-imidazo[4,5-c][1,5]naphthyridin-4-amine of Formula XVI with 3N HCl in ethanol at reflux temperature.

In step (8) of Reaction Scheme I, the hydroxyl group on a 1H-imidazo[4,5-c][1,5]naphthyridin-4-amine of Formula XVII is converted to an ester of Formula XVIII. The reaction is conveniently carried out by adding a sulfonyl chloride such as methanesulfonyl chloride to a solution of the hydroxy-substituted compound of Formula XVII in the presence of a base such as triethylamine. The reaction can be carried out in a suitable solvent such as pyridine or dichloromethane at 0° C.

In step (9) of Reaction Scheme 1, a 1H-imidazo[4,5-c][1,5]naphthyridin-4-amine of Formula XVIII is cyclized to a tetracyclic compound of Formula XIX. The reaction is carried out by heating a solution of the compound of Formula XVIII in a solvent such as 1,2-dichloroethane. The reaction can be carried out at an elevated temperature such as 60° C.

In step (10) of Reaction Scheme I, a tetracyclic compound of Formula XIX is reduced to a tetracyclic tertiary amine of Formula I. The reaction can be carried out by hydrogenation using a heterogeneous hydrogenation catalyst such as platinum(IV) oxide. The hydrogenation is conveniently carried out in a Parr apparatus in a suitable solvent such as trifluoroacetic acid. The reaction can be carried out at ambient temperature.

Reaction Scheme I

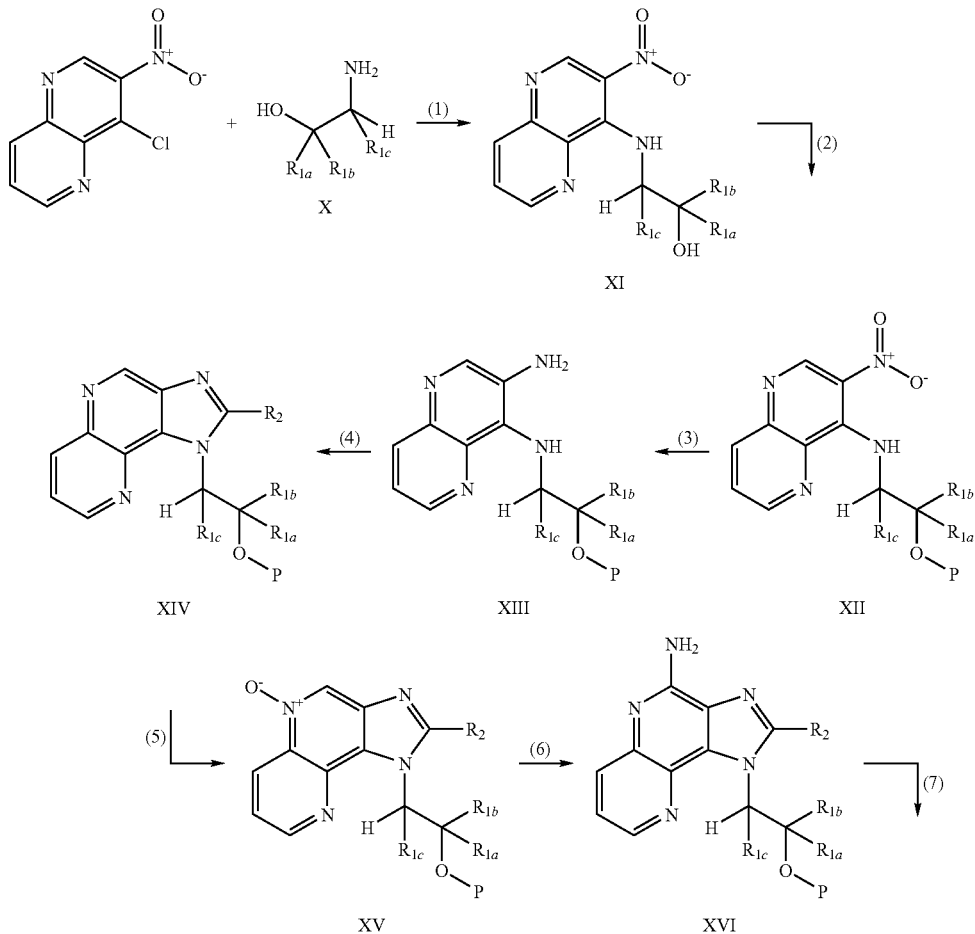

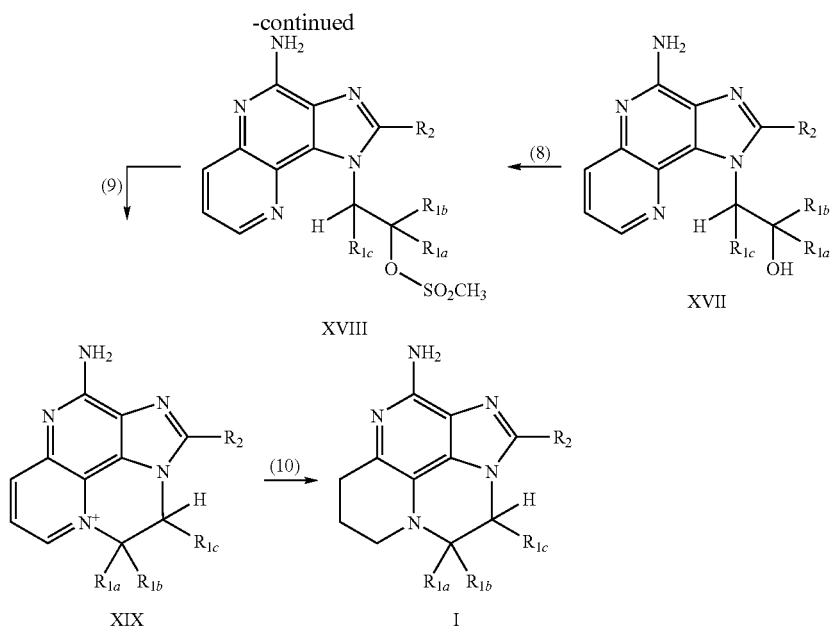

Compounds of the invention can also be prepared according to Reaction Scheme II, wherein $R_2$, $R_4$, Q and X are as defined above; and P is a hydroxy protecting group. In step (1) of Reaction Scheme II, 4-chloro-3-nitro[1,5]naphthyridine is treated with an amino alcohol of Formula Xa to provide a compound of Formula XX. Compounds of Formula Xa can be prepared by conventional synthetic methods from chiral, enantiomerically pure, commercially available starting materials such as L-ornithine hydrochloride and D-serine methyl ester hydrochloride. For example, the two amino groups of L-ornithine can be protected with two different protecting groups, such as a Boc group and a benzyloxycarbonyl group (Masiukiewicz, Org. Prep. Proced. Int. 34, 531-537, (2002)), and then the carboxylic acid group can be reduced to a hydroxy group. The hydroxy group can then be protected. A number of suitable hydroxy protecting groups can be used; in particular, protecting groups that would survive the reduction in step (2) are preferred. Suitable protecting groups include but are not limited to silyl groups such as the tert-butyl dimethylsilyl group. One of the amino groups can then be selectively deprotected for reaction in step (1). The methods described in Pickersgill, I. F. and Rapoport, H., J. Org. Chem., 65, pp. 4048-4057, (2000) and in Griesgraber, G. W. et al., International Publication No. WO 2006/083440 can also be used to prepare compounds of Formula Xa.

The reaction in step (1) is conveniently carried out by adding the amino alcohol of Formula Xa to a solution of 4-chloro-3-nitro[1,5]naphthyridine in a suitable solvent such as dichloromethane, optionally in the presence of a tertiary amine such as triethylamine. The reaction can be carried out at ambient temperature or at an elevated temperature such as, for example, the reflux temperature of the solvent.

In steps (2) through (6) of Reaction Scheme II, a compound of Formula XX is converted into a 1H-imidazo[4,5-c][1,5]naphthyridin-4-amine of Formula XXV using the methods described in steps (2) through (6) in Reaction Scheme I.

In step (7) of Reaction Scheme II, the hydroxy protecting group on a 1H-imidazo[4,5-c][1,5]naphthyridin-4-amine of Formula XXV is removed to reveal the hydroxy group in a product of Formula XXVI. The deprotection reaction can be carried out using a variety of conventional methods, depending on the protecting group used. When P is a silyl group such as tert-butyldimethylsilyl, the deprotection can be carried out by adding tetrabutylammonium fluoride to a 1H-imidazo[4,5-c][1,5]naphthyridin-4-amine of Formula XXV in a suitable solvent such as tetrahydrofuran (THF). The reaction can be carried out at ambient temperature or may be carried out at sub-ambient temperature, such as −78° C., and then warmed to ambient temperature.

In step (8) of Reaction Scheme II, the hydroxyl group on a 1H-imidazo[4,5-c][1,5]naphthyridin-4-amine of Formula XXVI is converted to an ester of Formula XXVII. The reaction is conveniently carried out by adding a sulfonyl chloride such as methanesulfonyl chloride to a solution of the hydroxy-substituted compound of Formula XXVI in the presence of a base such as triethylamine. The reaction can be carried out in a suitable solvent such as pyridine or dichloromethane at 0° C.

In step (9) of Reaction Scheme II, a 1H-imidazo[4,5-c][1,5]naphthyridin-4-amine of Formula XXVII is cyclized to a tetracyclic compound of Formula XXVIII. The reaction is carried out by heating a solution of the compound of Formula XXVII in a solvent such as 1,2-dichloroethane. The reaction can be carried out at an elevated temperature such as, for example, 60° C.

In step (10) of Reaction Scheme II, a tetracyclic compound of Formula XXVIII is reduced to a tetracyclic tertiary amine of Formula XXIX, which is a subgenus of Formula Ia. The reaction can be carried out by hydrogenation using a heterogeneous hydrogenation catalyst such as platinum(IV)oxide. The hydrogenation is conveniently carried Out in a Parr apparatus in a suitable solvent such as trifluoroacetic acid. When trifluoroacetic acid is used as the solvent, the tert-butoxycarbonyl (Boc) protecting group on the compound of Formula XXVIII is also removed to reveal an amino group in a compound of Formula XXIX. The reaction can be carried out at ambient temperature.

In step (11) of Reaction Scheme II, the amino group of a compound of Formula XXIX, revealed in step (10), or a salt thereof is converted to an amide, sulfonamide, sulfamide, or urea of Formula XXX, which is a subgenus of Formula Ia, using conventional methods. For example, a compound of Formula XXIX or salt thereof can react with an acid chloride of Formula $R_4C(O)Cl$ to provide a compound of Formula XXX in which Q is —C(O)—. In addition, a compound of Formula XXIX can react with a sulfonyl chloride of Formula $R_4S(O)_2Cl$ or a sulfonic anhydride of Formula $(R_4S(O)_2)_2O$ to provide a compound of Formula XXX in which Q is —S(O)$_2$—. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction is conveniently carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a solution of the compound of Formula XXIX in a suitable solvent such as chloroform, dichloromethane, N,N-dimethylformamide (DMF), or N,N-dimethylacetamide (DMA). Optionally, a base such as triethylamine, N,N-diisopropylethylamine, 1,8-diazabicyclo[5.4.0]undec-7-ene (DBU), or combinations thereof can be added. The reaction can be carried out at ambient temperature or a sub-ambient temperature such as 0° C.

Ureas of Formula XXX, where Q is —C(O)—NI-1-, can be prepared by reacting a compound of Formula XXIX or a salt thereof with isocyanates of Formula $R_4N=C=O$. Numerous isocyanates of Formula $R_4N=C=0$ are commercially available; others can be readily prepared using known synthetic methods. The reaction can be conveniently carried out by adding the isocyanate of Formula $R_4N=C=O$ to a solution of the compound of Formula XXIX in a suitable solvent such as DMF, chloroform, dichloromethane, or DMA. The reaction can be carried out at ambient temperature or a sub-ambient temperature such as 0° C. Alternatively, a compound of Formula XXIX can be treated with an isocyanate of Formula $R_4(CO)N=C=O$, a thioisocyanate of Formula $R_4N=C=S$, a sulfonyl isocyanate of Formula $R_4S(O)_2N=C=0$, or a carbamoyl chloride of Formula $R_4NH—C(O)Cl$ to provide a compound of Formula XXX, where Q is —C(O)—NH—C(O)—, —C(S)—NH—, —C(O)—NH—S(O)$_2$—, or —C(O)—NH—, respectively. Alternatively, a compound of Formula XXIX can be treated with a carbamoyl chloride of Formula

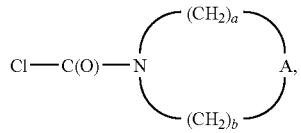

to provide a compound of Formula Ia, in which $R_{1c}$, is —X—$R_{5a}$, wherein $R_{5a}$ is

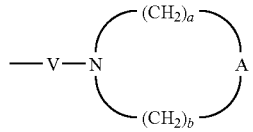

and V is NH—C(O)—.

Sulfamides of Formula XXX, where Q is —S(O)$_2$—N($R_8$)—, can be prepared by reacting a compound or salt of Formula XXIX with sulfuryl chloride to generate a sulfamoyl chloride in situ, and then reacting the sulfamoyl chloride with an amine of formula $HN(R_8)R_4$. Alternatively, sulfamides of Formula XXX can be prepared by reacting a compound of Formula XXIX with a sulfamoyl chloride of formula $R_4(R_8)N—S(O)_2Cl$. Many sulfonyl chlorides of Formula $R_4S(O)_2Cl$ and amines of Formula $HN(R_8)R_4$, and some sulfamoyl chlorides of formula $R_4(R_8)N—S(O)_2Cl$ are commercially available; others can be prepared using known synthetic methods.

Additionally, a compound or salt of Formula XXIX can be reacted with a chloroalkanesulfonyl chloride of Formula $C_1—R_7—S(O)_2Cl$ or a chloroalkanoyl chloride compound of formula $C_1—R_7—C(O)Cl$ to provide a compound of Formula Ia, wherein $R_{1c}$ is —X—$R_{5a}$ and $R_{5a}$ is a ring having the structure

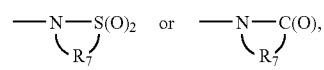

respectively. The reaction is preferably carried out by adding the chloroalkanesulfonyl chloride or chloroalkanoyl chloride to a solution of a compound of Formula XXIX in a suitable solvent such as dichloromethane in the presence of a base such as triethylamine or N,N-diisopropylethylamine. The intermediate chloroalkanesulfonamide or chloroalkanamide may optionally be isolated before treatment with a stronger base such as DBU at ambient temperature. If the intermediate chloroalkanesulfonamide or chloroalkanamide is isolated, the reaction with DBU can be carried out in a suitable solvent such as DMF.

A racemic mixture containing a compound of Formula XXX may be obtained in this scheme if a racemic amino alcohol is used instead of a compound of Formula Xa. A racemic mixture thus prepared can be resolved by methods known to one skilled in the art, for example, by reacting the racemic mixture with an enantiomerially pure sulfonic acid or carboxylic acid and selectively crystallizing a salt of one of the enantiomers from the mixture. Alternatively, the enantiomer of a compound of Formula XXX can be prepared using the enantiomer of the amino alcohol of Formula Xa in step (1) of Reaction Scheme II.

Reaction Scheme II

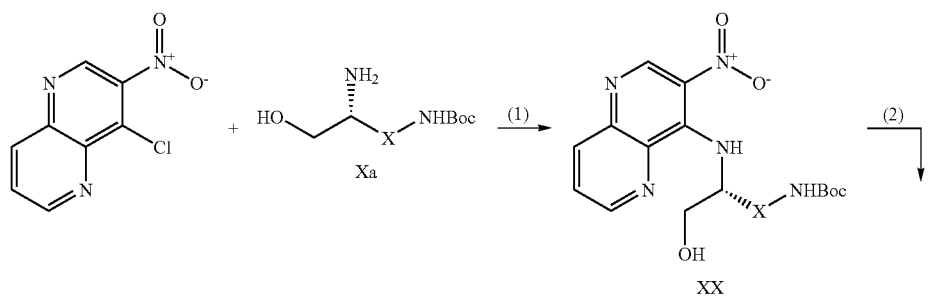

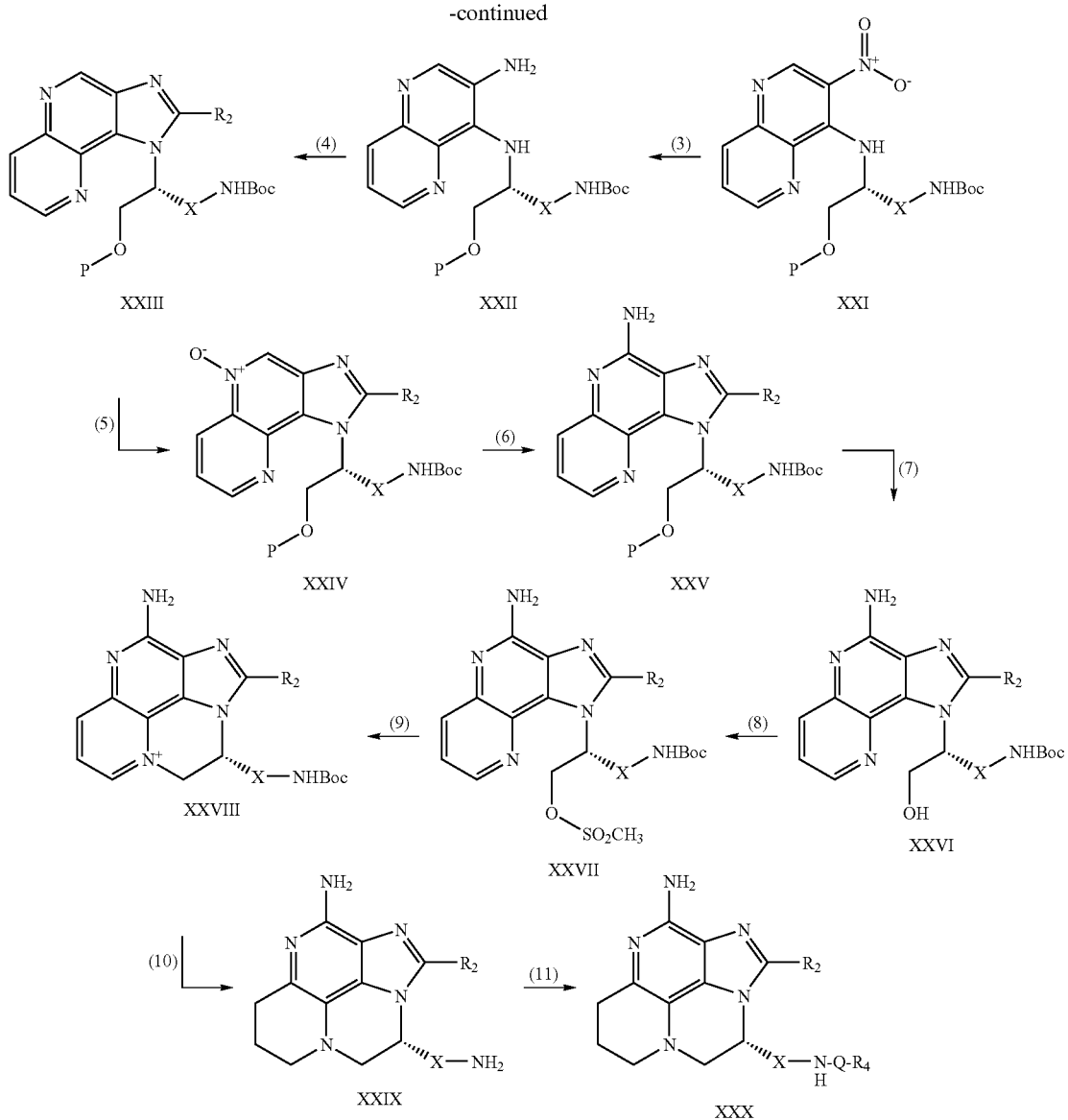
For certain embodiments, compounds of the invention can be prepared according to the methods described in steps (1) through (11) of Scheme II using a protected amino alcohol of the Formula Xb, Xc, Xd, or Xe in lieu of the protected amino alcohol of the Formula Xa in step (1).
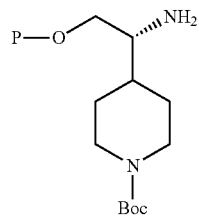
Xb
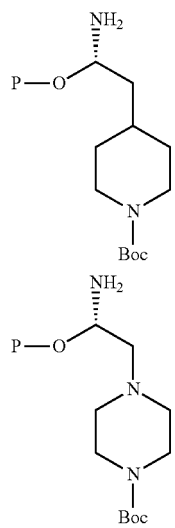
Xc
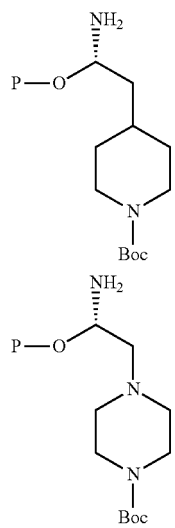
Xd

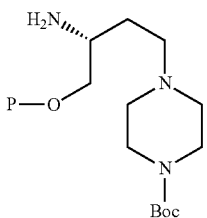

Compounds of Formula Xb can be prepared according to Reaction Scheme III. In step (1) of Reaction Scheme III, the N-(tert-butoxycarbonyl)-piperidine-4-carboxylate methyl ester of Formula XXXI is reduced to an aldehyde of Formula XXXII. The compound of Formula XXXI can be prepared according to known synthetic methods; for example, see the methods described in Carr, A. et al., *J. Org. Chem.*, 55, pp. 1399-1401 (1990). The reaction in step (1) of Scheme III is conveniently carried out by the addition of a solution of diisobutylaluminum hydride in hexanes to a solution of methyl ester XXXI in a solvent such as anhydrous diethyl ether. The reaction may be carried out at a reduced temperature such as −78° C.

In step (2) of Reaction Scheme III, the aldehyde group on the compound of Formula XXXII is converted to an olefin of Formula XXXIII. The reaction is carried out by forming the phosphorus ylid resulting from combining sodium hydride and methyltriphenylphosphonium bromide in a solvent such as tetrahydrofuran (THF) and adding the aldehyde of Formula XXXII to the phosphorus ylid solution. The ylid formation is carried out at an elevated temperature, such as the reflux temperature of the solvent, and the addition of aldehyde may be carried out at ambient temperature. The aldehyde may be conveniently added as a solution in a solvent such as THF.

In step (3) of Reaction Scheme III, the olefin group on the compound of Formula XXXIII is converted to a diol of Formula XXXIV. The reaction is carried out by combining the olefin compound of Formula XXXIII with AD-mix-α in a mixture of water and tert-butyl alcohol. The AD-mix-α reagent is commercially available and methods for its use in the asymmetric dihydroxylation of olefins are known (Sharpless et al., *J. Org. Chem.*, 57, pp. 2768-2771 (1992)). The reaction may be carried out at a sub-ambient temperature of, for example, 0° C.

In step (4) of Reaction Scheme III, the primary hydroxyl group of the compound of Formula XXXIV is protected using conventional techniques to provide the compound of Formula XXXV. Suitable protecting groups include but are not limited to silyl groups such as the tert-butyl dimethylsilyl group. The reaction is conveniently carried out by treating the compound of Formula XXXIV with tert-butyldimethylsilyl chloride in the presence of a base such as 2,6-lutidine. The reaction can be carried out in a suitable solvent such as dichloromethane at an initially sub-ambient temperature of 0° C. followed by allowing the reaction mixture to warm to ambient temperature.

In step (5) of Reaction Scheme III, the secondary hydroxyl group of the compound of Formula XXXV is converted to an ester of Formula XXXVI. The reaction is conveniently carried out by adding a sulfonyl chloride such as methanesulfonyl chloride to a solution of the hydroxyl-substituted compound of Formula XXXV in the presence of a base such as triethylamine. The reaction can be carried out in a suitable solvent such as dichloromethane at a sub-ambient temperature, such as 0° C.

In step (6) of Reaction Scheme III, the ester of Formula XXXVI is converted to an azide of Formula XXXVII. The reaction is carried out by adding sodium azide to a solution of the ester of Formula XXXVI. The reaction can be carried out in a suitable solvent such as N,N-dimethylformamide (DMF) at an elevated temperature, for example about 60° C. to 80° C.

In step (7) of Reaction Scheme III, the azido group of the compound of Formula XXXVII is reduced to an amino group. The reaction can be carried out by hydrogenation using a heterogeneous hydrogenation catalyst such as palladium on carbon. The hydrogenation is conveniently carried out in a Parr apparatus in a suitable solvent such as methanol. The reaction can be carried out at ambient temperature.

Reaction Scheme III

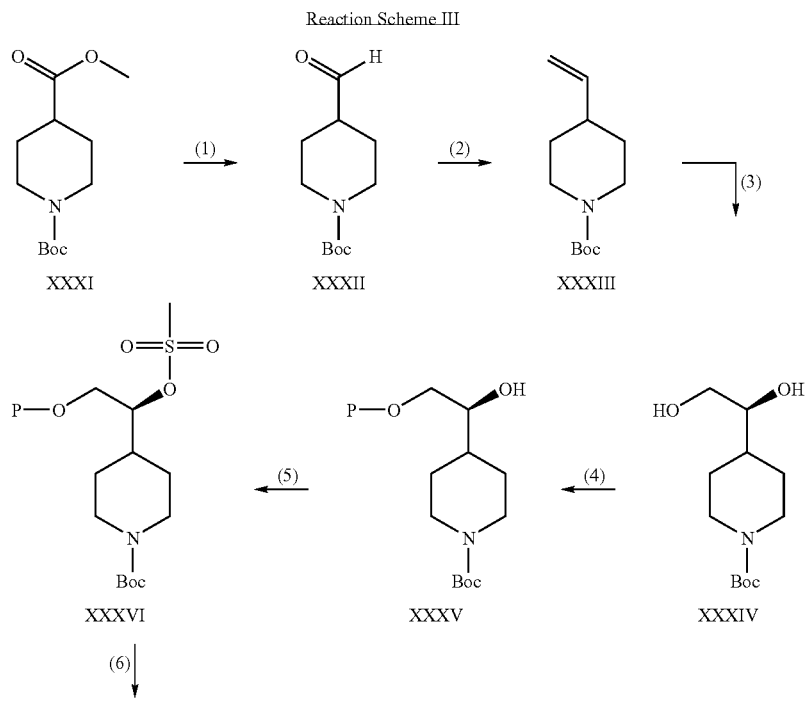

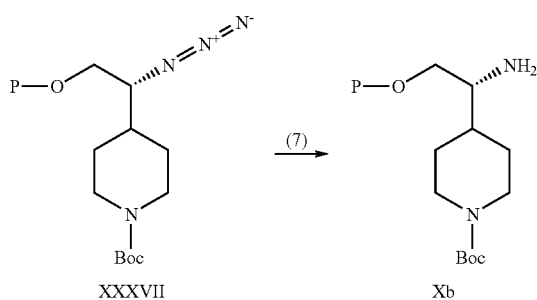

XXXVII → Xb

Compounds of Formula Xc can be prepared from an ester-containing compound of Formula XXXVIII by the methods in steps (1) through (7) of Reaction Scheme III. The ester-containing compound of Formula XXXVIII is commercially available.

XXXVIII

Compounds of Formula Xd can be prepared according to Reaction Scheme IV. In step (1) of Reaction Scheme IV, N-(tert-butoxycarbonyl)-piperazine is alkylated with (R)-3-bromo-1,2-propanediol acetonide to give an N-alkylated piperazine compound of Formula XLI. The (R)-3-bromo-1,2-propanediol acetonide of Formula XL can be prepared according to published procedures; for example, see the procedure in Kawakami et al., *J. Org. Chem.* 47, pp. 3581-3585 (1982). The reaction is carried out by heating N-(tert-butoxycarbonyl)-piperazine of Formula XXXIX together with (R)-3-bromo-1,2-propanediol acetonide of Formula XL in the presence of sodium iodide and a base such as sodium carbonate. The reaction may be carried out in a solvent such as 1,2-dimethoxyethane or acetonitrile at an elevated temperature, such as the reflux temperature of the solvent.

In step (2) of Reaction Scheme IV, the acetonide compound of Formula XLI is hydrolyzed to a diol of Formula XLII. The reaction can be carried out by warming the acetonide of Formula XLI in a mixture of acetone and 1N HCl. The reaction is carried out at an elevated temperature, such as the reflux temperature of the solvent. The hydrolysis reaction is accompanied by cleavage of the N-(tert-butoxycarbonyl) group from the compound of Formula XLI.

In step (3) of Reaction Scheme IV, the piperazine of Formula XLII is protected with a Boc group to give a compound of Formula XLIII. The reaction is carried out by adding di-tert-butyldicarbonate to the piperazine of Formula XLII in the presence of a base such as triethylamine. The reaction may be conveniently be carried out in a solvent such as dichloromethane or tetrahydrofuran (THF). The reaction may be carried out at ambient temperature.

In step (4) of Reaction Scheme IV, the primary hydroxyl group in the compound of Formula XLIII is protected using conventional techniques to provide the compound of Formula XXXV. Suitable protecting groups include but are not limited to silyl groups such as the tert-butyl dimethylsilyl group. The reaction is carried out using the method of step (4) in Reaction Scheme III.

In steps (5) through (7) of Reaction Scheme IV, the secondary hydroxyl group in a compound of Formula XLIV is converted to an amino group in a compound of Formula Xd, using the methods of steps (5) through (7) in Reaction Scheme III.

Reaction Scheme IV

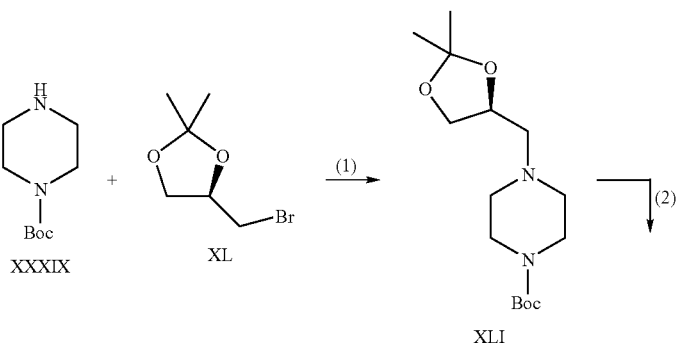

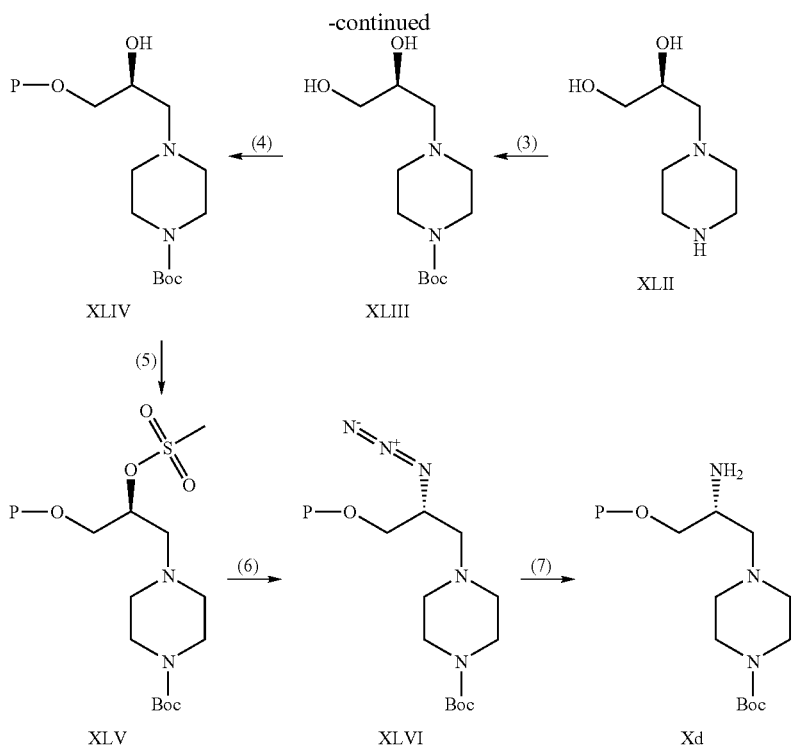

Compounds of Formula Xe can be prepared from a compound of Formula XLVII by the methods in steps (1) through (7) of Reaction Scheme IV. The compound of Formula XLVII can be prepared according to known synthetic methods; for example, see the methods described in Mori, et al., *Tetrahedron Lett.*, 25, pp. 6025-6026 (1984).

XLVII

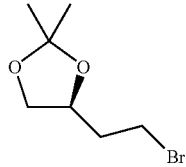

For certain embodiments, compounds of the invention can be prepared according to Reaction Scheme V, wherein $R_{1a}$, $R_{1b}$, $R_{1c}$, $R_2$, and G are as defined above. The amino group of a compound of Formula I can be converted by conventional methods to a functional group such as an amide, carbamate, urea, amidine, or another hydrolyzable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; wherein R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; each α-aminoacyl is an α-aminoacyl group derived from an α-amino acid selected from the group consisting of racemic, D-, and L-amino acids; Y' is selected from the group consisting of hydrogen, $C_{1-6}$ alkyl, and benzyl; $Y_0$ is selected from the group consisting of $C_{1-6}$ alkyl, carboxy-$C_{1-4}$ alkylenyl, amino-$C_{1-4}$ alkylenyl, mono-N—$C_{1-6}$ alkylamino-$C_{1-4}$ alkylenyl, and di-N,N—$C_{1-6}$alkylamino-$C_{1-4}$ alkylenyl; and $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl. Compounds of Formula I can be prepared according to the methods described above in Reaction Schemes I or II. Particularly useful compounds of Formula II are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at room temperature.

Reaction Scheme V

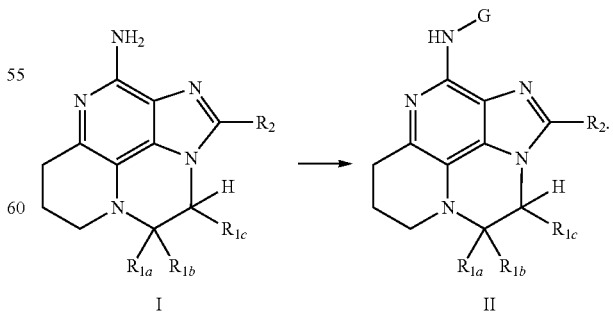

Compounds of the invention can also be prepared using variations of the synthetic routes shown in Reaction Schemes I and II that would be apparent to one of skill in the art, including variations described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (µg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations, syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders.

Cytokines whose production may be induced by the administration of compounds or salts of the invention generally include interferon-α (IFN-α) and tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases.

Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts described herein can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts described herein can also have an effect on the acquired immune response. For example, the production of the T helper type 1 (T$_H$1) cytokine IFN-γ may be induced indirectly and the production of the T helper type 2 (T$_H$2) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *pneumocystis car-*

*nii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients, and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction or inhibition of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention also provides a method of treating a viral infection in an animal and a method of treating a neoplastic disease in an animal comprising administering an effective amount of a compound or salt of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

The methods of the invention may be performed on any suitable subject. Suitable subjects include but are not limited to animals such as but not limited to humans, non-human primates, rodents, dogs, cats, horses, pigs, sheep, goats, or cows.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In some chromatographic separations described in the Examples below, the solvent mixture 80/18/2 v/v/v chloroform/methanol/concentrated ammonium hydroxide (CMA) was used as the polar component of the eluent. In these separations, CMA was mixed with chloroform in the indicated ratio.

In some chromatographic separations described in the Examples below, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

2-(Ethoxymethyl)-3,4,6,7-tetrahydro-5H-1,2a,4a,8-tetraazacyclopenta[cd]phenalen-9-amine

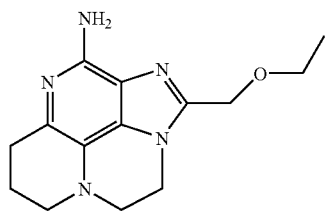

Part A

A solution of 3-nitro[1,5]naphthyridin-4-ol (9.14 g, 43.7 mmol) dissolved in 300 mL of $CH_2Cl_2$ was treated with ethanolamine (7.9 mL, 130 mmol) and the mixture was stirred under $N_2$. After 3 hours, the reaction mixture was concentrated to give a yellow solid. The yellow solid was treated with 200 mL of $H_2O$ and the suspension was heated to reflux, with stirring, for 10 minutes. The mixture was cooled in an ice bath. The resulting yellow solid was isolated by filtration, washed with cold $H_2O$ and dried with suction to give 2-[(3-nitro[1,5]naphthyridin-4-yl)amino]ethanol (10.02 g) as fine yellow crystals.

Part B

A solution of 2-[(3-nitro[1,5]naphthyridin-4-yl)amino]ethanol (6.34 g, 27.1 mmol) dissolved in 25 mL of pyridine was treated with tert-butyldimethylsilyl chloride (4.50 g, 29.8 mmol) and N,N-dimethylaminopyridine (331 mg, 2.71 mmol) and the mixture was stirred under $N_2$. After 3 hours, the reaction mixture was treated with 10 mL of methanol and then concentrated to give a yellow solid. The resulting solid was dissolved in 100 mL of ethyl acetate and washed with $H_2O$ (3×50 mL) and brine. The organic portion was dried over $Na_2SO_4$, filtered and concentrated under reduced pressure to give a yellow powder. Crystallization from 50 mL of 1:1 hexane/ethyl acetate gave 7.28 g of N-(2-{[tert-butyl(dimethyl)silyl]oxy}ethyl)-3-nitro[1,5]naphthyridin-4-amine as a yellow solid.

Part C

N-(2-{[tert-Butyl(dimethyl)silyl]oxy}ethyl)-3-nitro[1,5]naphthyridin-4-amine (2.36 g, 6.78 mmol) was dissolved in 50 mL of acetonitrile and the solution was placed in a pressure bottle. Platinum on carbon (5%, 200 mg) was then added and the reaction mixture was shaken under $H_2$ at 50 PSI ($3.4 \times 10^5$ Pa). After 3 hours, the reaction mixture was filtered through a pad of CELITE filter agent. The pad was rinsed with acetonitrile and the combined filtrates were concentrated under reduced pressure to give 2.12 g of $N^4$-(2-{[tert-butyl(dimethyl)silyl]oxy}ethyl)[1,5]naphthyridine-3,4-diamine as an orange solid.

Part D $N^4$-(2-{[tert-Butyl(dimethyl)silyl]oxy}ethyl)[1,5]naphthyridine-3,4-diamine (2.12 g, 6.67 mmol) was dissolved in 35 mL of anhydrous $CH_2Cl_2$ and the solution was cooled to 0° C. and stirred under $N_2$. Triethylamine (974 µL, 7.00 mmol) and ethoxyacetyl chloride (768 µL g, 7.00 mmol) were then added and the reaction mixture was stirred for 1 hour. The reaction mixture was then concentrated under reduced pressure to give a brown syrup. The brown syrup was dissolved in 50 mL of ethanol and treated with 4 mL of triethylamine. The mixture was heated to reflux for 3 days and then concentrated under reduced pressure. The resulting material was dissolved in 50 mL of $CH_2Cl_2$ and washed successively with $H_2O$ (2×50 mL) and brine (50 mL). The organic portion was dried over $Na_2SO_4$, filtered and concentrated under reduced pressure. Chromatography ($SiO_2$, 10-20% $CMA/CHCl_3$), gave 2.30 g of 1-(2-{[tert-butyl(dimethyl)silyl]oxy}ethyl)-2-(ethoxymethyl)-1H-imidazo[4,5-c][1,5]naphthyridine as a purple solid.

Part E 1-(2-{[tert-Butyl(dimethyl)silyl]oxy}ethyl)-2-(ethoxymethyl)-1H-imidazo[4,5-c][1,5]naphthyridine (2.30 g, 5.96 mmol) was dissolved in 30 mL of $CH_2Cl_2$ and treated with meta-chloroperbenzoic acid (MCPBA) (1.80 g, 57-86% purity). After stirring for 2 hours, the reaction mixture was treated with 25 mL of $CH_2Cl_2$ and 25 mL of 5% $Na_2CO_3$ solution and the layers were separated. The organic portion was then washed successively with $H_2O$ (20 mL) and brine (20 mL). The organic portion was dried over $Na_2SO_4$, filtered and concentrated under reduced pressure to give 2.40 g of 1-2-{[tert-butyl(dimethyl)silyl]oxy)ethyl}-2-(ethoxymethyl)-1H-imidazo[4,5-c][1,5]naphthyridine 5-oxide as a purple syrup.

Part F 1-(2-{[tert-Butyl(dimethyl)silyl]oxy}ethyl)-2-(ethoxymethyl)-1H-imidazo[4,5-c][1,5]naphthyridine 5-oxide (2.40 g, 5.97 mmol) was dissolved in 60 mL of $CH_2Cl_2$ and treated with 6 mL of concentrated aqueous $NH_4OH$ solution. The mixture was stirred rapidly and then p-toluenesulfonyl chloride (1.19 g, 6.27 mmol) was carefully added. Rapid stirring was continued for 1.5 hours. The reaction mixture was then treated with 50 mL of $CH_2Cl_2$ and 25 mL of $H_2O$. The layers were separated and the organic portion was washed successively with 2% $Na_2CO_3$ solution (2×25 mL), $H_2O$ and brine. The organic portion was dried over $Na_2SO_4$, filtered and concentrated under reduced pressure. Chromatography ($SiO_2$, 10-15% $CMA/CHCl_3$) gave 1-2-{[tert-butyl(dimethyl)silyl]oxy}ethyl)-2-(ethoxymethyl)-1H-imidazo[4,5-c][1,5]naphthyridin-4-amine (1.93 g) as a light-brown foam.

Part G 1-(2-{[tert-Butyl(dimethyl)silyl]oxy}ethyl)-2-(ethoxymethyl)-1H-imidazo[4,5-c][1,5]naphthyridin-4-amine (1.93 g, 4.81 mmol) was dissolved in 20 mL of ethanol and treated with 1.6 mL of 3 M HCl in ethanol and the mixture was heated to reflux. After 2 hours, the reaction mixture was concentrated under reduced pressure and the resulting residue was partitioned between 50 mL of $CHCl_3$ and 25 mL of dilute $NH_4OH$ solution. The layers were separated and the aqueous portion was extracted with additional $CHCl_3$ (12×20 mL). The combined organic portions were washed with 10 mL of brine, dried over $Na_2SO_4$, filtered and concentrated under reduced pressure. Chromatography ($SiO_2$, 25% $CMA/CHCl_3$) gave 2-[4-amino-2-(ethoxymethyl)-1H-imidazo[4,5-c][1,5]naphthyridin-1-yl]ethanol (1.93 g) as a light-yellow powder.

Part H

2-[4-Amino-2-(ethoxymethyl)-1H-imidazo[4,5-c][1,5]naphthyridin-1-yl]ethanol (865 mg, 3.01 mmol) was dissolved in 10 mL of anhydrous pyridine and treated with triethylamine (0.70 mL, 5.0 mmol). The reaction mixture was cooled to 0° C. under $N_2$ and treated with methanesulfonyl chloride (0.21 mL, 2.7 mmol). After stirring for 2 hours, the reaction mixture was concentrated under reduced pressure. The resulting syrup was dissolved in 30 mL of 1,2-dichloroethane and the mixture was heated to 60° C., under $N_2$, for 3 days. The reaction mixture was concentrated under reduced pressure and then concentrated from ethanol. The resulting material was dissolved in 10 mL of trifluoroacetic acid and the solution was placed in a pressure bottle. Platinum(IV) oxide (250 mg) was then added and the reaction mixture was shaken under $H_2$ at 50 PSI ($3.4 \times 10^5$ Pa) overnight. The reaction mixture was then filtered through a pad of CELITE filter agent. The pad was rinsed with a mixture of $CH_2Cl_2$ and 2-propanol. The filtrate was concentrated under reduced pressure and the resulting syrup was dissolved in 10 mL of $H_2O$. Concentrated $NH_4OH$ solution (2 mL) was added and the mixture was extracted with $CHCl_3$ (3×25 mL). The combined organic portions were dried over $Na_2SO_4$, filtered and concentrated under reduced pressure. The resulting material was treated with 10 mL of methanol and filtered to remove some insoluble material. The filtrate was concentrated to give a solid, which was crystallized from ethyl acetate with a small amount of methanol. The resulting crystals were isolated by filtration, rinsed with cold ethyl acetate and dried under vacuum overnight to give the title compound (192 mg) as golden crystals, m.p. 172-173° C. $^1$H NMR (300 MHz, DMSO-$d_6$) δ 5.53 (s, 2H), 4.65 (s, 2H), 4.31 (t, J=5.0 Hz, 2H), 3.49 (q, J=7.0 Hz, 1H), 3.09 (t, J=5.0 Hz, 2H), 2.92 (t, J=5.2 Hz, 2H), 2.59 (t, J=6.5 Hz, 2H), 2.07 (m, 2H), 1.13 (t, J=7.0 Hz, 3H); $^{13}$C NMR (125 MHz, DMSO-$d_6$) δ 147.3, 144.8, 131.3, 129.6, 123.8, 120.6, 65.6, 64.6, 49.4, 48.4, 43.9, 27.2, 22.8, 15.3; MS (ESI) m/z 274 (M+H)$^+$; Anal. calcd for $C_{14}H_{19}N_5O$: C, 61.52; H, 7.01; N, 25.62. Found: C, 61.53; H, 6.96; N, 25.90.

Example 2

2-(2-Methoxyethyl)-3,4,6,7-tetrahydro-5H-1,2a,4a,8-tetraazacyclopenta[cd]phenalen-9-amine

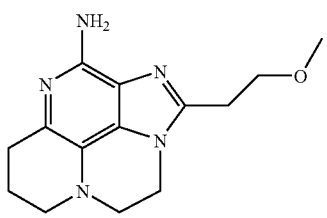

The title compound was prepared from $N^4$-(2-{[tert-butyl (dimethyl)silyl]oxy}ethyl)[1,5]naphthyridine-3,4-diamine and methoxypropionyl chloride using the methods described in Parts D through H of Example 1. Chromatography (SiO$_2$, 15% CMA/CHCl$_3$) of the final material gave a solid, which was dissolved in methanol and filtered to remove insoluble material. The filtrate was concentrated and crystallized from methanol to give off-white needles, m.p. 171-172° C. $^1$H NMR (300 MHz, DMSO-$d_6$) δ 5.40 (s, 2H), 4.26 (t, J=5.0 Hz, 2H), 3.70 (t, J=6.6 Hz, 2H), 3.25 (s, 3H), 3.08 (t, J=5.0 Hz, 2H), 3.02 (t, J=6.6 Hz, 2H), 2.92 (t, J=5.2 Hz, 2H), 2.58 (t, J=6.5 Hz, 2H), 2.06 (m, 2H); $^{13}$C NMR (125 MHz, DMSO-$d_6$) δ 148.3, 143.8, 13.0.5, 128.4, 123.6, 120.1, 70.0, 57.9, 49.0, 48.0, 42.9, 27.0, 26.7, 22.4; MS (ESI) m/z 274 (M+H)$^+$; Anal. calcd for $C_{14}H_{19}N_5O$: C, 61.52; H, 7.01; N, 25.62. Found: C, 60.70; H, 7.32; N, 26.00.

Example 3

2-Propyl-3,4,6,7-tetrahydro-5H-1,2a,4a,8-tetraazacyclopenta[cd]phenalen-9-amine

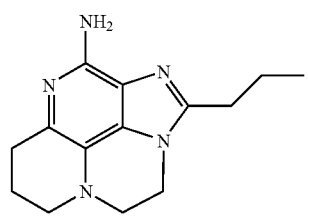

Part A $N^4$-(2-{[tert-Butyl(dimethyl)silyl]oxy}ethyl)[1,5]naphthyridine-3,4-diamine (57 mmol), trimethyl orthobutyrate (13.8 mL, 86.1 mmol), pyridine hydrochloride (0.5 g), and toluene (200 mL) were combined and heated at reflux for 2 hours. The reaction mixture was allowed to cool to ambient temperature and then subjected to an aqueous workup. The crude product was purified by automated flash chromatography using a HORIZON HPFC system (an automated high-performance flash purification product available from Biotage, Inc, Charlottesville, Va., USA) eluting with a gradient of ethyl acetate in hexanes to provide about 10 g of an oil which solidified. This material was triturated with hexanes containing a small amount of ethyl acetate to provide about 9.1 g of 1-(2-{[tert-butyl(dimethyl)silyl]oxy}ethyl)-2-propyl-1H-imidazo[4,5-c][1,5]naphthyridine.

Part B

The title compound was prepared from 1-(2-{[tert-butyl (dimethyl)silyl]oxy}ethyl)-2-propyl-1H-imidazo[4,5-c][1,5]naphthyridine using the methods described in Parts E through H of Example 1. The final compound was crystallized from ethyl acetate with a little methanol to give fine needles: m.p. 225-230° C. $^1$H NMR (300 MHz, DMSO-$d_6$) δ 5.39 (s, 2H), 4.24 (t, J=5.0 Hz, 2H), 3.08 (t, J=5.0 Hz, 2H), 2.92 (t, J=5.2 Hz, 2H), 2.74 (t, J=7.4 Hz, 2H), 2.58 (t, J=6.5 Hz, 2H), 2.06 (m, 2H), 1.74 (m, 2H), 0.95 (t, J=7.4 Hz, 3H); $^{13}$C NMR (125 MHz, DMSO-$d_6$) δ 151.0, 144.2, 130.9, 128.8, 124.0, 120.6, 49.4, 48.4, 43.2, 28.5, 27.1, 22.9, 21.1, 14.0; MS (ESI) m/z 258 (M+H)$^+$; Anal. calcd for $C_{14}H_{19}N_6$: C, 65.34; H, 7.44; N, 27.21. Found: C, 65.25; H, 7.36; N, 27.45.

Example 4

(3R)-2-(Ethoxymethyl)-3-methyl-3,4,6,7-tetrahydro-5H-1,2a,4a,8-tetraazacyclopenta[cd]phenalen-9-amine

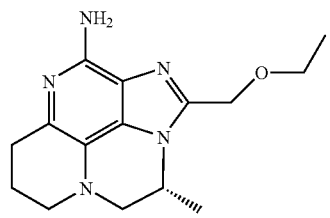

Part A

A solution of 4-chloro-3-nitro[1,5]naphthyridine (6.30 g, 30.1 mmol) dissolved in 150 mL of $CH_2Cl_2$ was treated with triethylamine (8.35 mL, 60.0 mmol) and (R)-2-aminopropanol (2.76 mL, 35.5 mmol) and the mixture was stirred under N₂. After 18 hours, the reaction mixture was concentrated to give a yellow solid. The yellow solid was combined with 150 mL of H₂O and the suspension was heated to reflux, with stirring, for 20 minutes. The mixture was cooled in an ice bath and the resulting yellow solid was isolated by filtration. The solid washed with cold H₂O and two 50 mL-portions of Et₂O and then dried with suction to give (2R)-2-[(3-nitro[1,5]naphthyridin-4-yl)amino]propan-1-ol (7.10 g) as a yellow powder.

Part B

The title compound was prepared using the methods described in Parts B through H of Example I with the following modification. In Part D, the imidazole formation was not complete. The isolated material, using the described conditions for Example 1, was dissolved in 20 mL of 7% NH₃ in methanol and the mixture was heated to 150° C. in a pressure vessel overnight. The reaction mixture was concentrated under reduced pressure and the resulting residue was dissolved in CH₂Cl₂ and washed with H₂O and brine. The organic portion was dried over Na₂SO₄, filtered and concentrated under reduced pressure. Chromatography (SiO₂, 2-10% methanol/CH₂Cl₂) gave 1-((1R)-2-{[tert-butyl(dimethyl)silyl]oxy}-1-methylethyl)-2-(ethoxymethyl)-1H-imidazo[4,5-c][1,5]naphthyridine as a purple oil. The synthesis was then completed using the methods described in Parts E through H of Example 1. Crystallization from ethyl acetate to gave the title compound as off-white crystals, m.p. 164.5-166.1° C. ¹H NMR (300 MHz, DMSO-d₆) δ 5.54 (s, 2H), 4.76 (m, 1H), 4.69 (d, J=12.6 Hz, 1H), 4.63 (d, J=12.6 Hz, 1H), 3.51 (q, J=7.0 Hz, 1H), 3.16-3.09 (m, 2H), 2.86 (dd, J=3.3, 11.4 Hz, 1H), 2.72-2.54 (m, 3H), 2.09 (m, 2H), 1.47 (d, J=6.6 Hz, 3H), 1.14 (t, J₇ 7.0 Hz, 3H); ¹³C NMR (125 MHz, DMSO-d₆) δ 146.3, 144.3, 130.4, 129.1, 123.3, 120.1, 65.1., 64.3, 54.9, 50.3, 47.9, 26.7, 22.4, 19.7, 14.8; MS (ESI) m/z 288 (M+H)⁺; Anal. calcd for C₁₅H₂₁N₅O: C, 62.70; H, 7.37; N, 24.57. Found: C, 62.55; H, 7.38; N, 24.53.

Example 5

(3S)-2-(Ethoxymethyl)-3-methyl-3,4,6,7-tetrahydro-5H-1,2a,4a,8-tetraazacyclopenta[cd]phenalen-9-amine

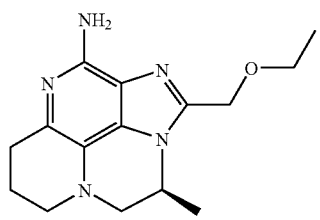

The title compound was prepared from 4-chloro-3-nitro[1,5]naphthyridine and (S)-2-aminopropanol using the methods described in Parts A and B of Example 4. Crystallization from ethyl acetate gave the title compound as off-white crystals, m.p. 164.1-165.6° C. MS (ESI) m/z 288 (M+H)⁺; Anal. calcd for C₁₅H₂₁N₅O: C, 62.70; H, 7.37; N, 24.57. Found: C, 62.52; H, 7.60; N, 24.57.

Example 6

2-(Ethoxymethyl)-4,4-dimethyl-3,4,6,7-tetrahydro-5H-1,2a,4a,8-tetraazacyclopenta[cd]phenalen-9-amine hydrochloride

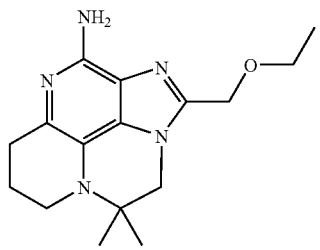

A solution of 1-[4-amino-2-(ethoxymethyl)-1H-imidazo[4,5-c][1,5]naphthyridin-1-yl]-2-methylpropan-2-ol (500 mg, 1.59 mmol) dissolved in 15 mL of anhydrous CH₂Cl₂ was treated with thionyl chloride (232 mL, 3.18 mmol). After 30 minutes, the reaction mixture was concentrated under reduced pressure. The resulting material was concentrated from ethanol and then dissolved in 15 mL of TFA. The mixture was placed in pressure flask and treated with 250 mg of PtO₂. The mixture was then shaken under H₂ at 50 PSI (3.4× 10⁵ Pa) for 3 hours. The reaction mixture was filtered through a pad of CELITE filter agent. The pad was rinsed with CH₂Cl₂ and 2-propanol and the combined filtrates were concentrated under reduced pressure to give a syrup. The syrup was dissolved in 50 mL of hot ethanol and crystals formed upon cooling. The crystals were isolated by filtration and were then partitioned between dilute NH₄OH solution (25 mL) and CH₂Cl₂ (25 mL). The organic portion was washed with additional dilute NH₄OH solution (2×), H₂O and brine. The organic portion was concentrated to give a syrup. Crystallization from HCl in ethanol gave the title compound as a yellow powder, m.p. 222-227° C. ¹H NMR (300 MHz, DMSO-d₆) δ 7.87 (s, 2H), 4.74 (s, 2H), 4.18 (s, 2H), 3.50 (q, J=7.0 Hz, 2H), 3.06 (t, J=5.1 Hz, 2H), 2.71 (t, J=6.2 Hz, 2H), 2.08 (m, 2H), 1.17 (s, 6H), 1.14 (t, J=7.0 Hz, 3H); ¹³C NMR (125 MHz, DMSO-d₆) δ 150.5, 143.9, 132.8, 121.3, 119.5, 119.3, 65.4, 63.7, 54.5, 54.4, 22.1, 20.9, 20.7, 14.8; MS (ESI) m/z 302 (M+H)³⁰; Anal. calcd for C₁₆H₂₃N₅O.HCl: C, 56.88; H, 7.16; N, 20.73; Cl, 10.51. Found: C, 56.61; H, 8.09; N, 20.51; Cl, 10.88.

Exemplary Compounds

Certain exemplary compounds, including some of those described above in the Examples, have the following Formulas (Ib, Ic, Id, Ie, If, Ig, or Ih) and the following R$_{1c-1}$ substituents, wherein each line of the table is matched with Formula Ib, Ic, Id, Ie, If, Ig, or Ih to represent a specific embodiment of the invention.

Ib

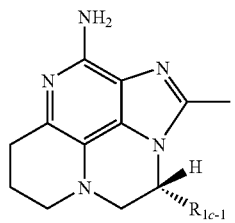

-continued

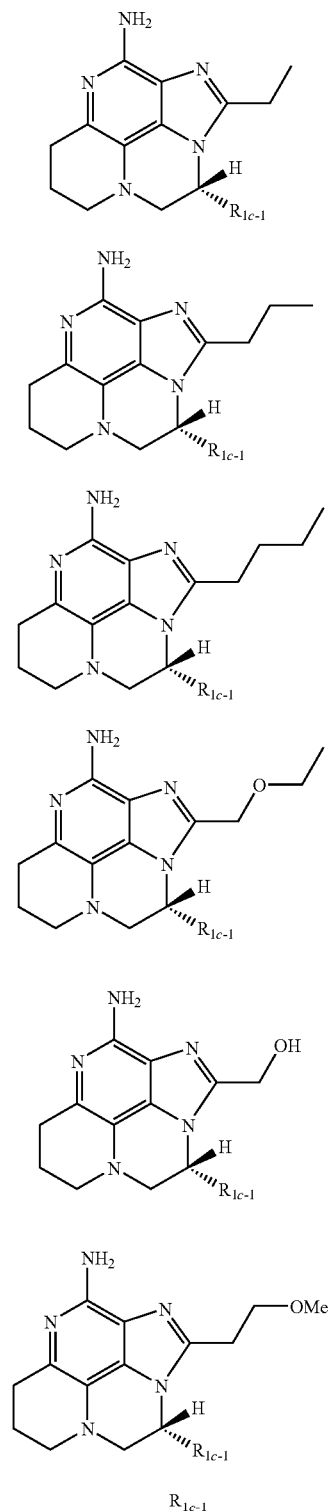

| $R_{1c\text{-}1}$ |
|---|
| methyl |
| isopropyl |
| 1-fluoro-1-methylethyl |
| 1-hydroxy-1-methylethyl |
| 1-hydroxyethyl |
| tetrahydro-2H-pyran-4-yl |

Certain exemplary compounds, including some of those described above in the Examples, have the following Formulas (Ii, Ij, Ik, Il, Im, In, or Io) and the following $X_a$ and $-Y_c-R_{4a}$ substituents, wherein each line of the table is matched with Formula Ii, Ij, Ik, Il, Im, In, or Io to represent a specific embodiment of the invention.

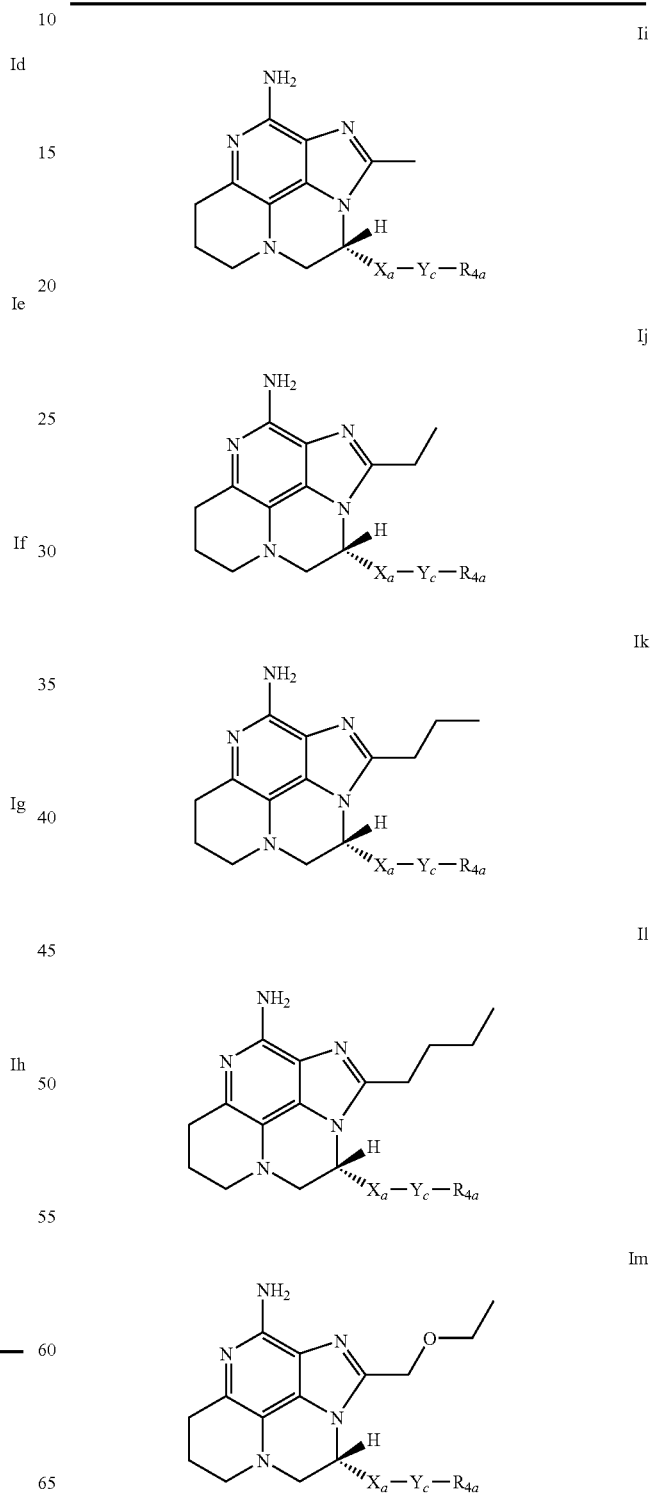

-continued

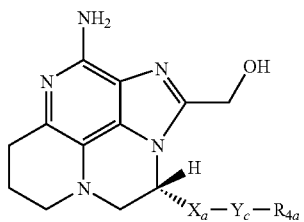

| $X_a$ | $-Y_c-R_{4a}$ |
|---|---|
| —CH$_2$— | —NH—S(O)$_2$—CH$_3$ |
| —CH$_2$— | 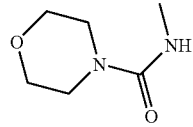 |
| —CH$_2$— | —NH—C(O)—CH(CH$_3$)$_2$ |
| —CH$_2$— | —NH—C(O)—CH$_3$ |
| —CH$_2$— | —NH—C(O)—NH—CH(CH$_3$)$_2$ |
| —CH$_2$— |  |
| —CH$_2$— | —NH—C(O)—N(CH$_3$)$_2$ |
| —(CH$_2$)$_2$— | —NH—S(O)$_2$—CH$_3$ |
| —(CH$_2$)$_2$— | 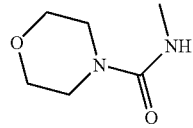 |
| —(CH$_2$)$_2$— | —NH—C(O)—CH(CH$_3$)$_2$ |
| —(CH$_2$)$_2$— | —NH—C(O)—CH$_3$ |
| —(CH$_2$)$_2$— | —NH—C(O)—NH—CH(CH$_3$)$_2$ |
| —(CH$_2$)$_2$— |  |
| —(CH$_2$)$_2$— | —NH—C(O)—N(CH$_3$)$_2$ |
| —(CH$_2$)$_3$— | —NH—S(O)$_2$—CH$_3$ |

-continued

| | | |
|---|---|---|
| —(CH$_2$)$_3$— | 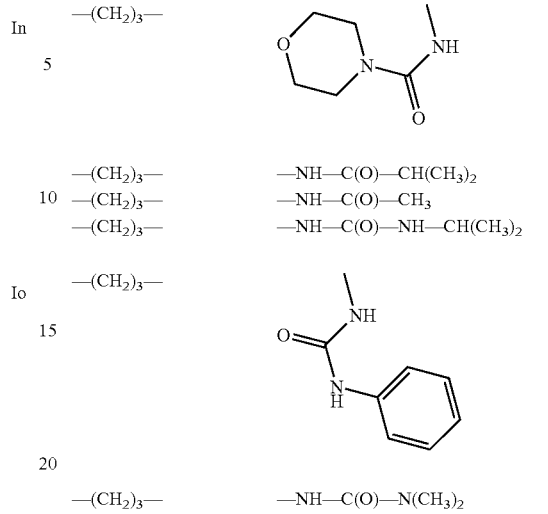 | In |
| —(CH$_2$)$_3$— | —NH—C(O)—CH(CH$_3$)$_2$ | |
| —(CH$_2$)$_3$— | —NH—C(O)—CH$_3$ | |
| —(CH$_2$)$_3$— | —NH—C(O)—NH—CH(CH$_3$)$_2$ | |
| —(CH$_2$)$_3$— | | Io |
| | | |
| —(CH$_2$)$_3$— | —NH—C(O)—N(CH$_3$)$_2$ | |

Certain exemplary compounds, including some of those described above in the Examples, have the following Formulas (Ip, Iq, Ir, Is, It, Iu, or Iv) and the following $X_{b\ and}$ -$Q_a$-$R_{4a}$ substituents, wherein each line of the table is matched with Formula Ip, Iq, Ir, Is, It, Iu, or Iv to represent a specific embodiment of the invention.

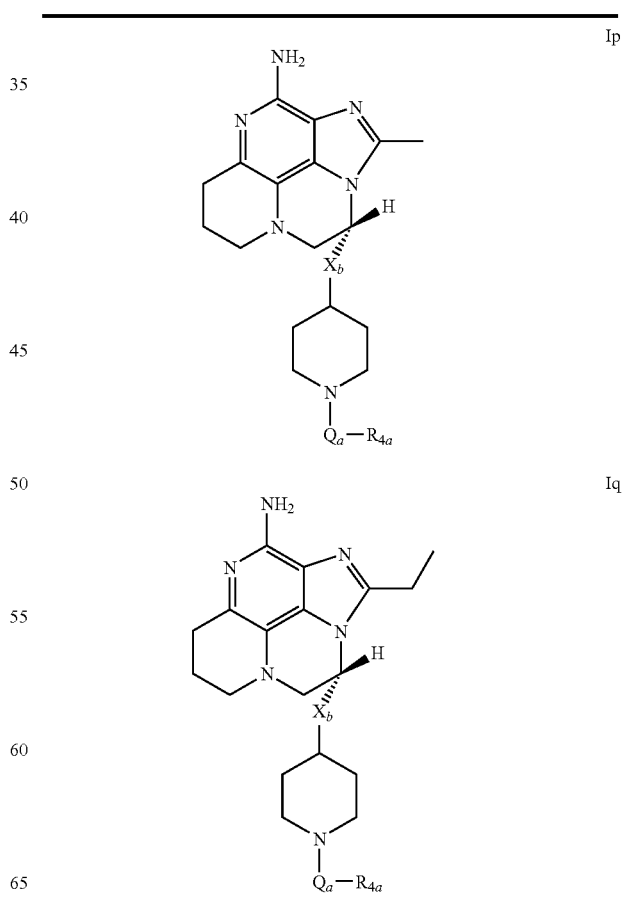

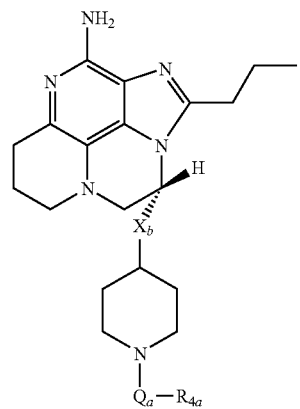

Ir

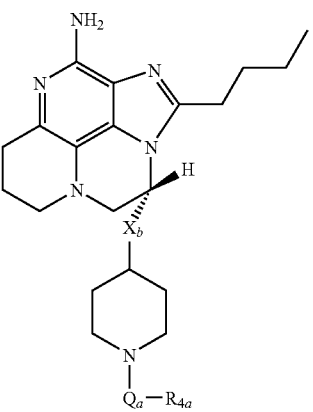

Is

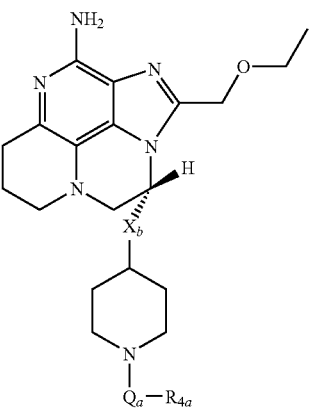

It

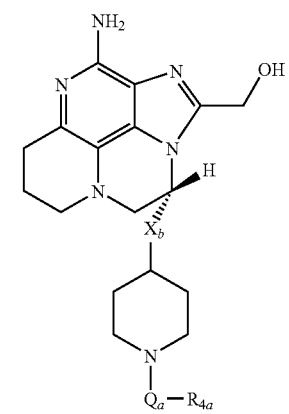

Iu

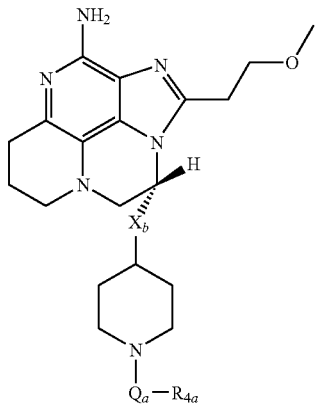

Iv

| $X_b$ | $-Q_a-R_{4a}$ |
|---|---|
| bond | —S(O)₂—CH₃ |
| bond | 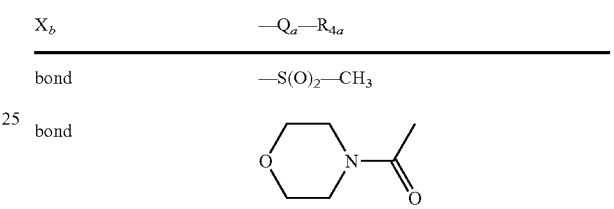 |
| bond | —C(O)—CH(CH₃)₂ |
| bond | —C(O)—CH₃ |
| bond | —C(O)—NH—CH(CH₃)₂ |
| bond | 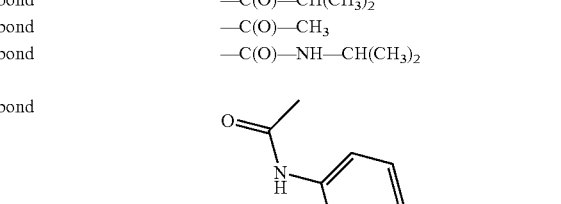 |
| bond | —C(O)—N(CH₃)₂ |
| —CH₂— | —S(O)₂—CH₃ |
| —CH₂— | 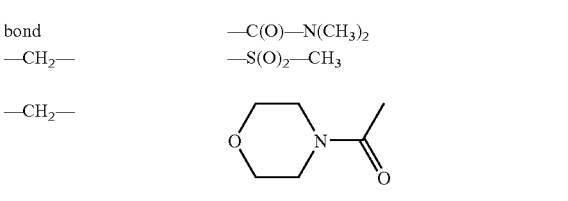 |
| —CH₂— | —C(O)—CH(CH₃)₂ |
| —CH₂— | —C(O)—CH₃ |
| —CH₂— | —C(O)—NH—CH(CH₃)₂ |
| —CH₂— | 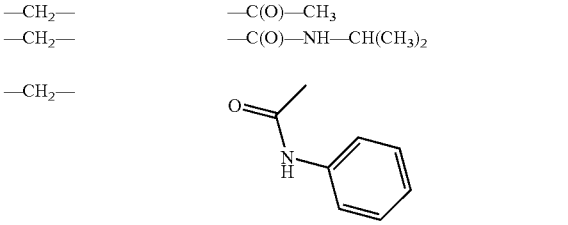 |
| —CH₂— | —C(O)—N(CH₃)₂ |

Certain exemplary compounds, including some of those described above in the Examples, have the following Formulas (Iw, Ix, Iy, Iz, Iba, Ibb, or Ibc) and the following $X_c$ and -$Q_a$-$R_{4a}$ substituents, wherein each line of the table is matched with Formula Iw, Ix, Iy, Iz, Iba, Ibb, or Ibc to represent a specific embodiment of the invention.

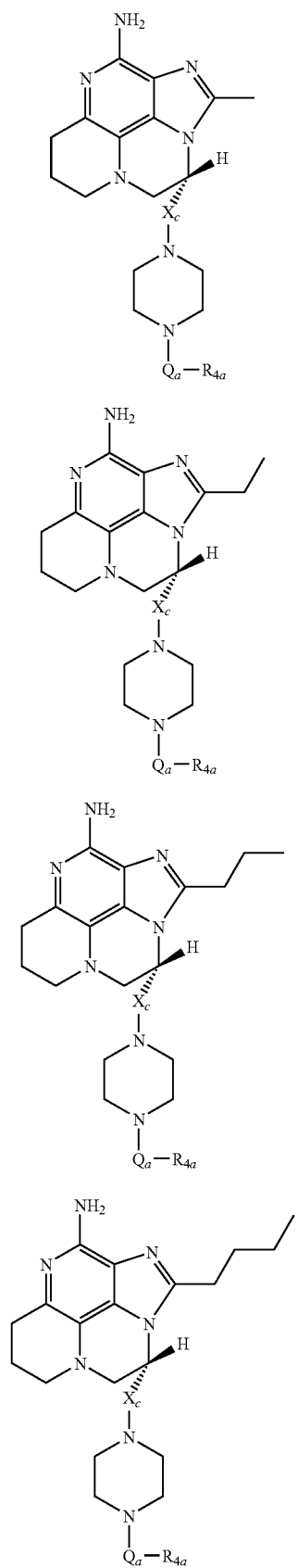
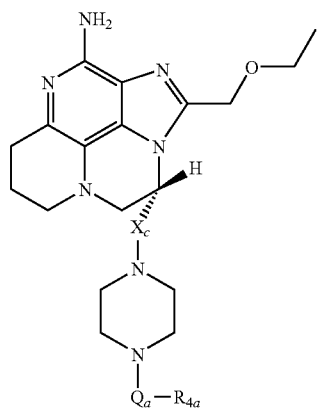
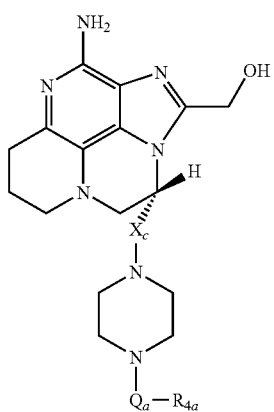
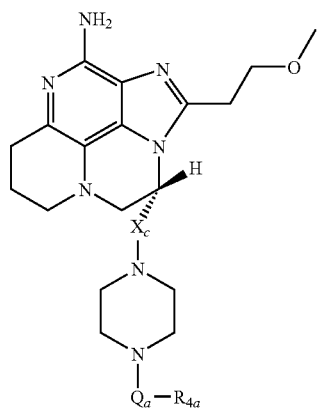
| $X_c$ | —$Q_a$—$R_{4a}$ |
|---|---|
| —CH$_2$— | —S(O)$_2$—CH$_3$ |
| —CH$_2$— | 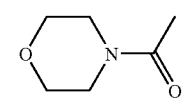 |
| —CH$_2$— | —C(O)—CH(CH$_3$)$_2$ |
| —CH$_2$— | —C(O)—CH$_3$ |
| —CH$_2$— | —C(O)—NH—CH(CH$_3$)$_2$ |

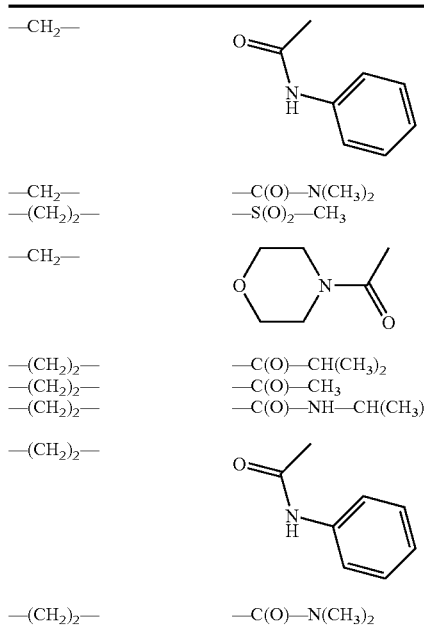

Compounds of the invention have been found to modulate cytokine biosynthesis by inducing the production of interferon α and/or tumor necrosis factor α in human cells when tested using one of the methods described below.

Cytokine Induction 1N Human Cells

An in vitro human blood cell system is used to assess cytokine induction. Activity is based on the measurement of interferon (α) and tumor necrosis factor (a) (IFN-α and TNF-α, respectively) secreted into culture media as described by Testerman et al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences, Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (a) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction In Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences, Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-α F (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A compound of the formula:

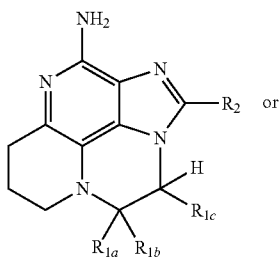

wherein:
- $R_{1a}$ and $R_{1b}$ are independently selected from the group consisting of hydrogen, $C_{1-6}$ alkyl, 1-hydroxy-1-methylethyl, 1-(methylsulfonylamino)-1-methylethyl, 3-(methylsulfonylamino)propyl and 1-fluoro-1-methylethyl; or $R_{1a}$ and $R_{1b}$, together with the carbon atom to which they are attached, form a ring selected from the group consisting of cyclopropane, cyclobutane, cyclopentane, cyclohexane, oxetane, tetrahydrofuran, and tetrahydropyran;
- $R_{1c}$ is selected from the group consisting of:
  —X—$R_4$,
  —X—Y—$R_4$,
  —X—Y—X'—Y—$R_4$, and
  —X—$R_5$;
- $R_2$ is selected from the group consisting of hydrogen, alkyl, alkoxyalkyl, and hydroxyalkyl;
- X is alkylene optionally interrupted by one or more —O— groups, and optionally substituted by a hydroxy or methoxy group;
- X' is selected from the group consisting of alkylene, arylene, heteroarylene, and heterocyclylene wherein the alkylene group can be optionally interrupted or terminated by arylene, heteroarylene or heterocyclylene and optionally interrupted by one or more —O— groups;
- Y is selected from the group consisting of:
  —O—,
  —S(O)$_{0-2}$—,
  —S(O)$_2$—N($R_8$)—,
  —C($R_6$)—,
  —C($R_6$)—O—,
  —O—C($R_6$)—,
  —O—C(O)—O—,
  —N($R_8$)-Q-,
  —C($R_6$)—N($R_8$)—,
  —O—C($R_6$)—N($R_8$)—,
  —C($R_6$)—N(O$R_9$)—,
  —O—N($R_8$)-Q-,
  —O—N=C($R_4$)—,
  —C(=N—O—$R_8$)—, and
  —CH(—N(—O—$R_8$)-Q-$R_4$)—,
- $R_4$ is selected from the group consisting of hydrogen, alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl and heterocyclyl, oxo; with the proviso that when $R_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when $R_4$ is heterocyclyl, then the one or more substituents may also be independently selected from the group consisting of arylalkylenyl, and aminocarbonyl;
- $R_5$ is selected from the group consisting of:

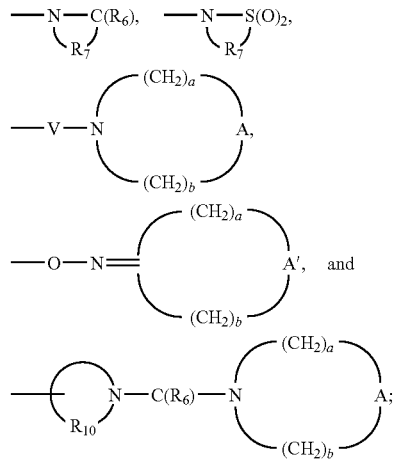

- $R_6$ is selected from the group consisting of =O and =S;
- $R_7$ is $C_{2-7}$ alkylene;
- $R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
- $R_9$ is selected from the group consisting of hydrogen and alkyl;
- $R_{10}$ is $C_{3-8}$ alkylene;
- A is selected from the group consisting of —CH$_2$—, —O—, —C(O)—, —S(O)$_{0-2}$—, and —N(-Q-$R_4$)—;
- A' is selected from the group consisting of —O—, —S(O)$_{0-2}$—, —N(-Q-$R_4$)—, and —CH$_2$—;
- Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
- V is selected from the group consisting of —C($R_6$)—, —O—C($R_6$)—, —N($R_8$)—C($R_6$)—, and —S(O)$_2$—;
- W is selected from the group consisting of a bond, —C(O)—, and —S(O)$_2$—; and
- a and b are independently integers from 1 to 6 with the proviso that a+b is ≦7;

with the proviso that X can also be a bond when:
R$_4$ is bonded to X; or
Y is bonded to X and Y is —C(R$_6$)—, —C(R$_6$)—O—, —C(R$_6$)—N(R$_8$)—, —C(R$_6$)—N(OR$_9$)—, —C(=N—O—R$_8$)—, or —CH(—N(—O—R$_8$)-Q-R$_4$)—; or
R$_5$ is bonded to X and R$_5$ is

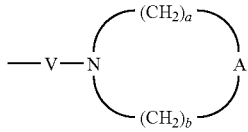

wherein V is —C(R$_6$)— or

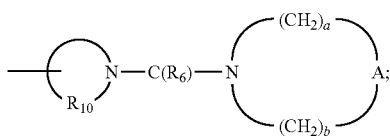

or a pharmaceutically acceptable salt thereof.

2. The compound or salt of claim 1 wherein R$_{1a}$ and R$_{1b}$ are independently selected from the group consisting of hydrogen, C$_{1-6}$ alkyl, 1-hydroxy-1-methylethyl, 1-(methylsulfonylamino)-1-methylethyl, 3-(methylsulfonylamino)propyl and 1-fluoro-1-methylethyl.

3. The compound or salt of claim 1 wherein R$_{1a}$ and R$_{1b}$ join together to form a ring selected from the group consisting of cyclopropane, cyclobutane, cyclopentane, cyclohexane, oxetane, tetrahydrofuran, and tetrahydropyran.

4. The compound or salt of claim 1 wherein R$_{1c}$ is selected from the group consisting of —X—R$_4$, —X—Y—R$_4$ and —X—Y—X'—Y'—R$_4$.

5. The compound or salt of claim 1 wherein R$_2$ is selected from the group consisting of hydrogen, alkyl, alkoxyalkyl, and hydroxyalkyl.

6. The compound or salt of claim 4 wherein R$_{1c}$ is —X—R$_4$.

7. The compound or salt of claim 6 wherein R$_4$ in —X—R$_4$ is alkyl which is unsubstituted or substituted by one or more substituents selected from the group consisting of halogen, hydroxy, and alkoxy.

8. The compound or salt of claim 5 wherein R$_2$ is selected from the group consisting of methyl, ethyl, n-propyl, n-butyl, ethoxymethyl, hydroxymethyl, and 2-methoxyethyl).

9. A pharmaceutical composition comprising a therapeutically effective amount of a compound or salt of claim 1 and a pharmaceutically acceptable carrier.

10. A method of inducing cytokine biosynthesis in an animal comprising administering an effective amount of a compound or salt of claim 1 to the animal.

11. A compound of the formula:

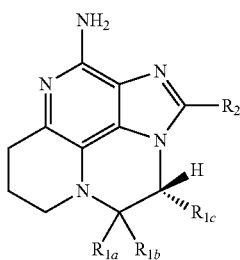

Ia wherein:
R$_{1a}$ and R$_{1b}$ are independently selected from the group consisting of hydrogen, C$_{1-6}$ alkyl, 1-hydroxy-1-methylethyl, 1-(methylsulfonylamino)-1-methylethyl, 3-(methylsulfonylamino)propyl and 1-fluoro-1-methylethyl; or R$_{1a}$ and R$_{1b}$, together with the carbon atom to which they are attached, form a ring selected from the group consisting of cyclopropane, cyclobutane, cyclopentane, cyclohexane, oxetane, tetrahydrofuran, and tetrahydropyran;
R$_{1c}$ is selected from the group consisting of:
—X—R$_4$,
—X—Y—R$_4$,
—X—Y—X'—Y—R$_4$, and
—X—R$_5$;
R$_2$ is selected from the group consisting of hydrogen, alkyl, alkoxyalkyl, and hydroxyalkyl;
X is alkylene optionally interrupted by one or more —O— groups, and optionally substituted by a hydroxy or methoxy group;
X' is selected from the group consisting of alkylene, arylene, heteroarylene, and heterocyclylene wherein the alkylene group can be optionally interrupted or terminated by arylene, heteroarylene or heterocyclylene and optionally interrupted by one or more —O— groups;
Y is selected from the group consisting of:
—O—,
—S(O)$_{0-2}$,
—S(O)$_2$—N(R$_8$)—,
—C(R$_6$)—,
—C(R$_6$)—O—,
—O—C(R$_6$)—,
—O—C(O)—O—,
—N(R$_8$)-Q-,
—C(R$_6$)—N(R$_8$)—,
—O—C(R$_6$)—N(R$_8$)—,
—C(R$_6$)—N(OR$_9$)—,
—O—N(R$_8$)-Q-,
—O—N=C(R$_4$)—,
—C(=N—O—R$_8$)—, and
—CH(—N(—O—R$_8$)-Q-R$_4$)—,
R$_4$ is selected from the group consisting of hydrogen, alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl; alkoxy; hydroxyalkyl; haloalkyl; haloalkoxy; halogen; hydroxy; mercapto; cyano; aryl; aryloxy; arylalkyleneoxy; heteroaryl; heteroaryloxy; heteroarylalkyleneoxy; heterocyclyl; amino; alkylamino; dialkylamino; (dialkylamino)alkyleneoxy; and, in the case of alkyl and heterocyclyl, oxo; with the proviso that when R$_4$ is aryl, arylalkylenyl, heteroaryl, or heteroarylalkylenyl, then the one or more substituents may also be independently selected from the group consisting of arylalkylenyl, alkylarylenyl, alkoxyarylenyl, haloarylenyl, alkylsulfonylamino, arylsulfonylamino, alkylcarbonylamino, arylcarbonylamino, alkylaminocarbonylamino, arylaminocarbonylamino, heteroarylsulfonylamino, heteroarylcarbonylamino, heteroarylaminocarbonylamino, alkoxycarbonylamino, and aryloxycarbonylamino; and with the further proviso that when R$_4$ is heterocyclyl, then the one or more substituents may also be independently selected from the group consisting of arylalkylenyl, and aminocarbonyl;

$R_5$ is selected from the group consisting of:

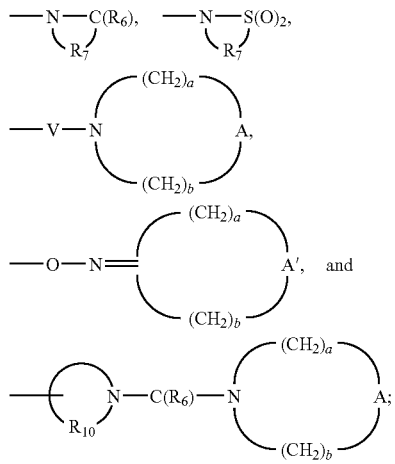

$R_6$ is selected from the group consisting of =O and =S;
$R_7$ is $C_{2-7}$ alkylene;
$R_8$ is selected from the group consisting of hydrogen, $C_{1-10}$ alkyl, $C_{2-10}$ alkenyl, hydroxy-$C_{1-10}$ alkylenyl, $C_{1-10}$ alkoxy-$C_{1-10}$ alkylenyl, aryl-$C_{1-10}$ alkylenyl, and heteroaryl-$C_{1-10}$ alkylenyl;
$R_9$ is selected from the group consisting of hydrogen and alkyl;
$R_{10}$ is $C_{3-8}$ alkylene;
A is selected from the group consisting of —$CH_2$—, —O—, —C(O)—, —S(O)$_{0-2}$—, and —N(-Q-$R_4$)—;
A' is selected from the group consisting of —O—, —S(O)$_{0-2}$—, —N(-Q-$R_4$)—, and —$CH_2$—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—; and
a and b are independently integers from 1 to 6 with the proviso that a+b is ≦7;
with the proviso that X can also be a bond when:
  $R_4$ is bonded to X; or
  Y is bonded to X and Y is —C($R_6$)—, —C($R_6$)—O—, —C($R_6$)—N($R_8$)—, —C($R_6$)—N(O$R_9$)—, —C(=N—O—$R_8$)—, or —CH(—N(—O—$R_8$)-Q-$R_4$)—; or $R_5$ is bonded to X and $R_5$ is

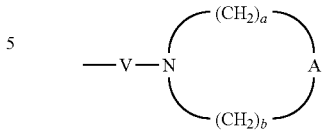

wherein V is —C($R_6$)— or

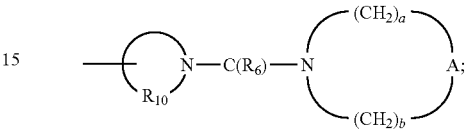

or a pharmaceutically acceptable salt thereof.

12. The compound or salt of claim 11 wherein $R_{1a}$ and $R_{1b}$ are independently selected from the group consisting of hydrogen, $C_{1-6}$ alkyl, 1-hydroxy-1-methylethyl, 1-(methylsulfonylamino)-1-methylethyl, 3-(methylsulfonylamino) propyl and 1-fluoro-1-methylethyl.

13. The compound or salt of claim 11 wherein $R_{1a}$ and $R_{1b}$ join together to form a ring selected from the group consisting of cyclopropane, cyclobutane, cyclopentane, cyclohexane, oxetane, tetrahydrofuran, and tetrahydropyran.

14. The compound or salt of claim 11 wherein $R_{1c}$ is selected from the group consisting of —X—$R_4$, —X—Y—$R_4$ and —X—Y—X'—Y'—$R_4$.

15. The compound or salt of claim 11 wherein $R_2$ is selected from the group consisting of hydrogen, alkyl, alkoxyalkyl, and hydroxyalkyl.

16. The compound or salt of claim 14 wherein $R_{1c}$ is —X—$R_4$.

17. The compound or salt of claim 16 wherein $R_4$ in —X—$R_4$ is alkyl which is unsubstituted or substituted by one or more substituents selected from the group consisting of halogen, hydroxy, and alkoxy.

18. The compound or salt of claim 15 wherein $R_2$ is selected from the group consisting of methyl, ethyl, n-propyl, n-butyl, ethoxymethyl, hydroxymethyl, and 2-methoxyethyl.

19. A pharmaceutical composition comprising a therapeutically effective amount of a compound or salt of claim 11 and a pharmaceutically acceptable carrier.

20. A method of inducing cytokine biosynthesis in an animal comprising administering an effective amount of a compound or salt of claim 11 to the animal.

* * * * *